US012612554B2

(12) United States Patent
Ma et al.

(10) Patent No.: US 12,612,554 B2
(45) Date of Patent: Apr. 28, 2026

(54) LIQUID CRYSTAL ALIGNING AGENT, LIQUID CRYSTAL ALIGNMENT FILM, AND DISPLAY SUBSTRATE

(71) Applicants: HEFEI XINSHENG OPTOELECTRONICS TECHNOLOGY CO., LTD., Hefei (CN); BOE TECHNOLOGY GROUP CO., LTD., Beijing (CN)

(72) Inventors: Jian Ma, Beijing (CN); Wenming Ren, Beijing (CN); Chengyong Zhan, Beijing (CN); Ran Zhang, Beijing (CN)

(73) Assignees: HEFEI XINSHENG OPTOELECTRONICS TECHNOLOGY CO., LTD., Hefei (CN); BOE TECHNOLOGY GROUP CO., LTD., Beijing (CN)

( * ) Notice: Subject to any disclaimer, the term of this patent is extended or adjusted under 35 U.S.C. 154(b) by 770 days.

(21) Appl. No.: 17/803,000

(22) PCT Filed: Aug. 10, 2021

(86) PCT No.: PCT/CN2021/111782

§ 371 (c)(1),
(2) Date: Aug. 29, 2022

(87) PCT Pub. No.: WO2022/057522

PCT Pub. Date: Mar. 24, 2022

(65) Prior Publication Data

US 2023/0103608 A1 Apr. 6, 2023

(30) Foreign Application Priority Data

Sep. 16, 2020 (CN) ........................ 202010975445.7

(51) Int. Cl.
*C09K 19/56* (2006.01)
*C07D 307/60* (2006.01)
(Continued)

(52) U.S. Cl.
CPC ............ *C09K 19/56* (2013.01); *C07D 307/60* (2013.01); *C08G 73/10* (2013.01); *C08L 79/08* (2013.01); *G02F 1/1337* (2013.01)

(58) Field of Classification Search
CPC ...... C09K 19/56; C08G 73/10; C07D 307/60; C08L 79/08; G02F 1/1337
(Continued)

(56) References Cited

FOREIGN PATENT DOCUMENTS

| | | | |
|---|---|---|---|
| CN | 101024773 | A | 8/2007 |
| CN | 102959461 | A | 3/2013 |

(Continued)

OTHER PUBLICATIONS

Teleshov et al., “Synthesis and properties of hydroquinone-and quinone-containing polypyromellitimides”, Polymer Science U.S. S.R., vol. 14, Issue 1, 1972, pp. 168-175.

*Primary Examiner* — Ruiyun Zhang
(74) *Attorney, Agent, or Firm* — Dority & Manning, P.A.

(57) ABSTRACT

A liquid crystal aligning agent includes polymer(s) from at least one of polyamic acid and group of polyimides by ring closure thereof. The acid includes a first segment structure formed by first dianhydride of formula (I) and first diamine of formula (II) or (III). $X_1$ is an amorphous first soft segment. L is single bond, double bond, divalent or trivalent hydrocarbon group having 1 to 3 Cs. $Y_1$ is single bond, O, NH, S, unsaturated double bond(s), or aliphatic, aromatic, heterocyclic or fused ring. One $A_1$ and one $A_2$, combined with $Y_1$, are each C. Remaining $A_1$s and $A_2$s are each CH, CR or N. $Z_1$ is aliphatic, aromatic, heterocyclic or fused ring. $A_3$s and $A_4$s are each CH, CR or N. Neither of numbers of
(Continued)

Ns in the $A_1$s, $A_2$s, $A_3$s and $A_4$s is more than two, $R_1$, $R_2$ and R are each hydrogen or aliphatic hydrocarbon group.

17 Claims, 5 Drawing Sheets

(51) Int. Cl.
*C08G 73/10* (2006.01)
*C08L 79/08* (2006.01)
*G02F 1/1337* (2006.01)

(58) Field of Classification Search
USPC .......................................................... 428/1.2
See application file for complete search history.

(56) References Cited

FOREIGN PATENT DOCUMENTS

| | | | | | |
|---|---|---|---|---|---|
| CN | 103387833 | A | | 11/2013 | |
| CN | 103911163 | A | | 7/2014 | |
| CN | 106916307 | A | | 7/2017 | |
| CN | 107089956 | A | | 8/2017 | |
| CN | 107557023 | A | | 1/2018 | |
| CN | 109937380 | A | | 6/2019 | |
| CN | 110499164 | A | * | 11/2019 | ............. C08G 73/10 |
| JP | 2003313180 | A | * | 11/2003 | ........... A61L 17/145 |
| JP | 2019174800 | A | | 10/2019 | |
| TW | 201934727 | A | | 9/2019 | |

* cited by examiner

LIQUID CRYSTAL ALIGNING AGENT, LIQUID CRYSTAL ALIGNMENT FILM, AND DISPLAY SUBSTRATE

CROSS-REFERENCE TO RELATED APPLICATIONS

This application is a national phase entry under 35 USC 371 of International Patent Application No. PCT/CN2021/111782 filed on Aug. 10, 2021, which claims priority to Chinese Patent Application No. 202010975445.7 filed on Sep. 16, 2020, which are incorporated herein by reference in their entirety.

TECHNICAL FIELD

The present disclosure relates to the field of display technologies, and in particular, to a liquid crystal aligning agent, a liquid crystal alignment film, and a display substrate.

BACKGROUND

Liquid crystal display devices are display devices currently used on a large scale. They have advantages of low costs, light weight and small thickness, fast display speed and the like, and are technically mature in both theoretical research and practical process.

SUMMARY

In an aspect, a liquid crystal aligning agent is provided. The liquid crystal aligning agent includes at least one polymer selected from at least one of a polyamic acid and a group of polyimides obtained by ring closure of the polyamic acid. The polyamic acid includes a first segment structure formed by reacting a first dianhydride represented by a following formula (I) with a first diamine represented by a following formula (II) or formula (III).

(I)

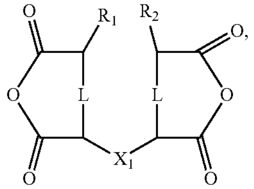

(II)

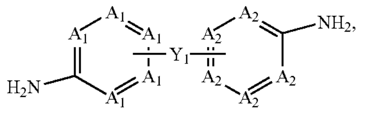

and (III)

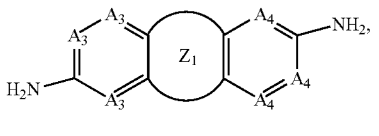

in which $X_1$ in the first dianhydride is a first soft segment, and the first soft segment is an amorphous segment; and L is any one selected from a single bond, a double bond and a divalent or trivalent hydrocarbon group having 1 to 3 carbon atoms; in the first diamine represented by the formula (II), $Y_1$ is any one selected from the single bond, O, NH, S, one or more unsaturated double bonds, a substituted or unsubstituted aliphatic ring, a substituted or unsubstituted aromatic ring, a substituted or unsubstituted heterocyclic ring and a substituted or unsubstituted fused ring; C is selected as each of a single $A_1$ and a single $A_2$, and the single $A_1$ and the single $A_2$ are both combined with $Y_1$; remaining $A_1$s and remaining $A_2$*s* are each any one independently selected from CH, CR and N, and neither of a number of Ns in the remaining $A_1$s and a number of Ns in the remaining $A_2$s is more than two.

In the first diamine represented by the formula (III), $Z_1$ is any one selected from the substituted or unsubstituted aliphatic ring, the substituted or unsubstituted aromatic ring, the substituted or unsubstituted heterocyclic ring and the substituted or unsubstituted fused ring, and $A_3$s and $A_4$s are each any one independently selected from CH, CR and N, and neither of a number of Ns in the $A_3$s and a number of Ns in the $A_4$s is more than two.

$R_1$, $R_2$ and R are each any one independently selected from hydrogen and an aliphatic hydrocarbon group.

In some embodiments, if a structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if a structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, then the first soft segment is any one selected from a hydrophilic segment and a segment including at least one hydrophilic group.

If the structure represented by the formula (II) is selected as the first diamine, and $Y_1$ is any one selected from the substituted aliphatic ring, the substituted aromatic ring, the substituted heterocyclic ring and the substituted fused ring, then at least one substituent group in $Y_1$ is any one selected from a hydrophobic group and a hydrophilic group, and the first soft segment is any one selected from the hydrophilic segment and the segment including the at least one hydrophilic group, or then the hydrophilic group is selected as the at least one substituent group in $Y_1$, and the first soft segment is any one selected from a hydrophobic segment, a segment including at least one hydrophobic group, the hydrophilic segment and the segment including the at least one hydrophilic group, or then one of the at least one substituent group in $Y_1$ and the first soft segment is any one selected from the hydrophilic segment and the segment including the at least one hydrophilic group, and another is any one selected from the hydrophobic segment and the segment including the at least one hydrophobic group.

If the structure represented by the formula (III) is selected as the first diamine, and $Z_1$ is any one selected from the substituted aliphatic ring, the substituted aromatic ring, the substituted heterocyclic ring and the substituted fused ring, then at least one substituent group in $Z_1$ is any one selected from the hydrophobic group and the hydrophilic group, and the first soft segment is any one selected from the hydrophilic segment and the segment including the at least one hydrophilic group, or then the hydrophilic group is selected as the at least one substituent group in $Z_1$, and the first soft segment is any one selected from the hydrophobic segment, the segment including the at least one hydrophobic group, the hydrophilic segment and the segment including the at least one hydrophilic group, or then one of the at least one substituent group in $Z_1$ and the first soft segment is any one selected from the hydrophilic segment and the segment including the at least one hydrophilic group, and another is any one selected from the hydrophobic segment and the segment including the at least one hydrophobic group.

In some embodiments, the first soft segment is any one selected from a hydrophobic segment and a segment including at least one hydrophobic group. A structure represented by the formula (II) is selected as the first diamine, and $Y_1$ is any one selected from the aromatic ring, the heterocyclic ring and the fused ring, in each of which at least one carbon atom is substituted, and at least one substituent group is any one selected from a hydrophilic group and a hydrocarbon group having 1 to 3 carbon atoms and having at least one hydrophilic group.

In some embodiments, in the first diamine, $Y_1$ is bonded to a para-position of an amino group, and a benzene ring in which a single carbon atom is substituted is selected as $Y_1$, and a substituent group is an alcoholic hydroxyl group having 1 to 3 carbon atoms.

In some embodiments, the first soft segment is a substituted or unsubstituted alkylene segment having 10 to 20 carbon atoms.

In some embodiments, the first dianhydride has an asymmetrical structure, or the first soft segment includes asymmetrical branches.

In some embodiments, the polyamic acid further includes a second segment structure formed by reacting a second dianhydride represented by a following formula (IV) with the first diamine.

(IV)

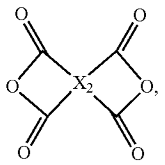

in which $X_2$ in the second dianhydride is any one selected from an aliphatic ring, an aromatic ring, a heterocyclic ring and a fused ring.

In some embodiments, a following formula is selected as a structure of $X_2$, in which $R_3$ and $R_4$ are each any one independently selected from hydrogen and the aliphatic hydrocarbon group.

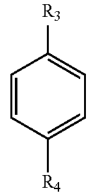

In some embodiments, a molar ratio of the first dianhydride to the second dianhydride is in a range from 10:90 to 90:10, inclusive.

In some embodiments, the polyamic acid further includes a third segment structure formed by reacting a second diamine represented by a following formula (V) with the first dianhydride.

(V)

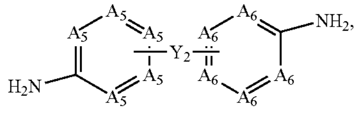

in which $Y_2$ in the second diamine is a second soft segment; C is selected as each of a single $A_5$ and a single $A_6$, and the single $A_5$ and the single $A_6$ are both combined with $Y_2$; remaining $A_5$s and remaining $A_6$s are each any one independently selected from CH, CR and N, and neither of a number of Ns in the remaining $A_5$s and a number of Ns in the remaining $A_6$s is more than two; and R is any one selected from hydrogen and the aliphatic hydrocarbon group.

In some embodiments, if a structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if a structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, then at least one of the first soft segment and the second soft segment is any one selected from a hydrophilic segment and a segment including at least one hydrophilic group.

If the structure represented by the formula (II) is selected as the first diamine, and $Y_1$ is any one selected from the substituted aliphatic ring, the substituted aromatic ring, the substituted heterocyclic ring and the substituted fused ring, then a hydrophilic group is selected as at least one substituent group in $Y_1$, and the first soft segment and the second soft segment are each any one independently selected from a hydrophobic segment, a segment including at least one hydrophobic group, the hydrophilic segment and the segment including the at least one hydrophilic group, or then a hydrophobic group is selected as the at least one substituent group in $Y_1$, and at least one of the first soft segment and the second soft segment is any one selected from the hydrophilic segment and the segment including the at least one hydrophilic group, and another is any one selected from the hydrophobic segment and the segment including the at least one hydrophobic group, or then one or two of the at least one substituent group in $Y_1$, the first soft segment and the second soft segment are each any one selected from the hydrophilic segment and the segment including the at least one hydrophilic group, and remaining two are each or a remaining one is any one selected from the hydrophobic segment and the segment including the at least one hydrophobic group.

If the structure represented by the formula (III) is selected as the first diamine, and $Z_1$ is any one selected from the substituted aliphatic ring, the substituted aromatic ring, the substituted heterocyclic ring and the substituted fused ring, then the hydrophilic group is selected as at least one substituent group in $Z_1$, and the first soft segment and the second soft segment are each any one independently selected from the hydrophobic segment, the segment including the at least one hydrophobic group, the hydrophilic segment and the segment including the at least one hydrophilic group, or then the hydrophobic group is selected as the at least one substituent group in $Z_1$, and at least one of the first soft segment and the second soft segment is any one selected from the hydrophilic segment and the segment including the at least one hydrophilic group, and another is any one selected from the hydrophobic segment and the segment including the at least one hydrophobic group, or then one or two of the at least one substituent group in $Z_1$, the first soft segment and the second soft segment are each any one selected from the hydrophilic segment and the segment including the at least one hydrophilic group, and remaining two are each or a remaining one is any one selected from the hydrophobic segment and the segment including the at least one hydrophobic group.

In some embodiments, the second soft segment is a substituted or unsubstituted alkylene segment having 5 to 12 carbon atoms.

In some embodiments, a molar ratio of the first diamine to the second diamine is in a range from 10:90 to 90:10, inclusive.

In another aspect, a liquid crystal aligning agent is provided. The liquid crystal aligning agent includes at least one polymer selected from at least one of a polyamic acid and a group of polyimides obtained by ring closure of the polyamic acid. The polyamic acid includes a first segment structure formed by a first dianhydride represented by a following formula (I) and a first diamine represented by a following formula (II) or formula (III), a second segment structure formed by a second dianhydride represented by a following formula (IV) and the first diamine, a third segment structure formed by a second diamine represented by a following formula (V) and the first dianhydride, and a fourth segment structure formed by the second diamine represented by the following formula (V) and the second dianhydride. Alternatively, the polyamic acid includes at least two segment structures of the third segment structure formed by the first dianhydride represented by the following formula (I) and the second diamine represented by the following formula (V), the fourth segment structure formed by reacting the second dianhydride represented by the following formula (IV) with the second diamine represented by the following formula (V), and the second segment structure formed by the second dianhydride represented by the following formula (IV) and the first diamine represented by the following formula (II) or formula (III).

(I)

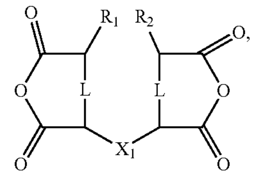

(II)

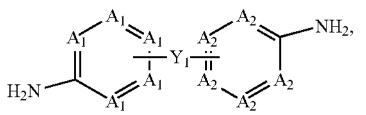

(III)

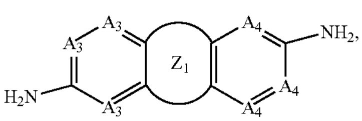

(IV)

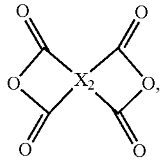

and

-continued (V)

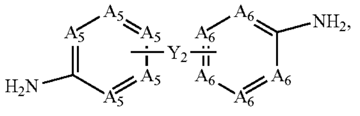

in which $X_1$ in the first dianhydride is a first soft segment, $Y_2$ in the second diamine is a second soft segment, and at least one of the first soft segment and the second soft segment is an amorphous segment; L in the first dianhydride is any one selected from a single bond, a double bond and a divalent or trivalent hydrocarbon group having 1 to 3 carbon atoms; $X_2$ in the second dianhydride is any one selected from a substituted or unsubstituted aliphatic ring, a substituted or unsubstituted aromatic ring, a substituted or unsubstituted heterocyclic ring and a substituted or unsubstituted fused ring; in the first diamine represented by formula (II), $Y_1$ is any one selected from the single bond, O, NH, S, one or more unsaturated double bonds, and the substituted or unsubstituted aliphatic ring, the substituted or unsubstituted aromatic ring, the substituted or unsubstituted heterocyclic ring and the substituted or unsubstituted fused ring; C is selected as each of a single $A_1$ and a single $A_2$, and the single $A_1$ and the single $A_2$ are both combined with $Y_1$; remaining $A_1$s and remaining $A_2$s are each any one independently selected from CH, CR and N, and neither of a number of Ns in the remaining $A_1$s and a number of Ns in the remaining $A_2$s is more than two; in the first diamine represented by formula (III), $Z_1$ is any one selected from the substituted or unsubstituted aliphatic ring, the substituted or unsubstituted aromatic ring, the substituted or unsubstituted heterocyclic ring and the substituted or unsubstituted fused ring, and $A_3$s and $A_4$s are each any one independently selected from CH, CR and N, and neither of a number of Ns in the $A_3$s and a number of Ns in the $A_4$s is more than two; in the second diamine, C is selected as each of a single $A_5$ and a single $A_6$, and the single $A_5$ and the single $A_6$ are both combined with $Y_2$; remaining $A_5$s and remaining $A_6$s are each any one independently selected from CH, CR and N, and neither of a number of Ns in the remaining $A_5$s and a number of Ns in the remaining $A_6$s is more than two; $R_1$, $R_2$ and R are each any one independently selected from hydrogen and an aliphatic hydrocarbon group.

In some embodiments, in a case where the polyamic acid includes the third segment structure formed by the first dianhydride represented by the formula (I) and the second diamine represented by the formula (V), and the fourth segment structure formed by reacting the second dianhydride represented by the formula (IV) with the second diamine represented by the formula (V), if $X_2$ in the second dianhydride is any one selected from the unsubstituted aliphatic ring, the unsubstituted aromatic ring, the unsubstituted heterocyclic ring and the unsubstituted fused ring, then the first soft segment and the second soft segment are each any one independently selected from a hydrophilic segment, a hydrophobic segment, a segment including at least one hydrophilic group and a segment including at least one hydrophobic group; and if $X_2$ in the second dianhydride is any one selected from the substituted aliphatic ring, the substituted aromatic ring, the substituted heterocyclic ring and the substituted fused ring, then at least one substituent group in $X_2$ is any one selected from a hydrophobic group and a hydrophilic group, and the first soft segment and the second soft segment are each any one independently selected from the hydrophilic segment and the segment including the at least one hydrophilic group, or then the hydrophobic group is selected as the at least one substituent group in $X_2$, and one of the first soft segment and the second soft segment is any one selected from the hydrophilic segment and the segment including the at least one hydrophilic group, and another is any one selected from the hydrophobic segment and the segment including the at least one hydrophobic group, or then one or two of the at least one substituent group in $X_2$, the first soft segment and the second soft segment are each any one selected from the hydrophilic segment and the segment including the at least one hydrophilic group, and remaining two are each or a remaining one is any one selected from the hydrophobic segment and the segment including the at least one hydrophobic group.

In a case where the polyamic acid includes the fourth segment structure formed by reacting the second dianhydride represented by the formula (IV) with the second diamine represented by the formula (V), and the second segment structure formed by the second dianhydride represented by the formula (IV) and the first diamine represented by the formula (II) or formula (III), if a structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if a structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the unsubstituted aliphatic ring, the unsubstituted aromatic ring, the unsubstituted heterocyclic ring and the unsubstituted fused ring, then the second soft segment is any one selected from a hydrophilic segment and a segment including at least one hydrophilic group; if the structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the substituted aliphatic ring, the substituted aromatic ring, the substituted heterocyclic ring and the substituted fused ring, then the hydrophilic group is selected as at least one substituent group in $X_2$, and the second soft segment is any one selected from the hydrophobic segment, the segment including the at least one hydrophobic group, the hydrophilic segment and the segment including the at least one hydrophilic group, or then the hydrophobic group is selected as the at least one substituent group in $X_2$, and the second soft segment is any one selected from the hydrophilic segment and the segment including the at least one hydrophilic group, or then at least one of the at least one substituent group in $X_2$ and the second soft segment is any one selected from the hydrophilic segment and the segment including the at least one hydrophilic group, and another is any one selected from the hydrophobic segment and the segment including the at least one hydrophobic group; if the structure represented by the formula (II) is selected as the first diamine, and $Y_1$ is any one selected from the substituted aliphatic ring, the substituted aromatic ring, the substituted heterocyclic ring and the substituted fused ring, or if the structure represented by the formula (III) is selected as the first diamine, and $Z_1$ is any one selected from the substituted aliphatic ring, the substituted aromatic ring, the substituted heterocyclic ring and the substituted fused ring, and $X_2$ is any one selected from the unsubstituted aliphatic ring, the unsubstituted aromatic ring, the unsubstituted heterocyclic ring and the unsubstituted fused ring, then at least one substituent group in $Y_1$ or $Z_1$ is the hydrophilic group, and the second soft segment is any one selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the second soft segment is any one selected from the hydrophilic segment and the segment including the at least one hydrophilic group, or then at least one of the at least one substituent group in $Y_1$ or $Z_1$ and the second soft segment is any one selected from the hydrophilic segment and the segment including the at least one hydrophilic group, and another is any one selected from the hydrophobic segment and the segment including the at least one hydrophobic group; and if the structure represented by the formula (II) is selected as the first diamine, and $Y_1$ is any one selected from the substituted aliphatic ring, the substituted aromatic ring, the substituted heterocyclic ring and the substituted fused ring, or if the structure represented by the formula (III) is selected as the first diamine, and $Z_1$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then the at least one substituent group in $Y_1$ or $Z_1$ is the hydrophilic group, and the at least one substituent group in $X_2$ is any one selected from the hydrophilic group and the hydrophobic group, and the second soft segment is any one selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the hydrophilic group is selected as the at least one substituent group in $X_2$, and the second soft segment is any one selected from the hydrophobic segment, the segment including the at least one hydrophobic group, the hydrophilic segment and the segment including the at least one hydrophilic group, or then the hydrophobic group is selected as each of the at least one substituent group in $Y_1$ or $Z_1$ and the at least one substituent group in $X_2$, and the second soft segment is any one selected from the hydrophilic segment and the segment including the at least one hydrophilic group, or then at least one of the at least one substituent group in $Y_1$ or $Z_1$, the at least one substituent group in $X_2$ and the second soft segment is any one selected from the hydrophilic segment and the segment including the at least one hydrophilic group, and remaining two are each or a remaining one is any one selected from the hydrophobic segment and the segment including the at least one hydrophobic group.

In a case where the polyamic acid includes the third segment structure formed by the first dianhydride represented by the formula (I) and the second diamine represented by the formula (V), and the second segment structure formed by the second dianhydride represented by the formula (IV) and the first diamine represented by the formula (II) or formula (III), or in a case where the polyamic acid includes the first segment structure formed by reacting the first dianhydride represented by the formula (I) with the first diamine represented by the formula (II) or formula (III), the second segment structure formed by reacting the second dianhydride represented by the formula (IV) with the first diamine, the third segment structure formed by reacting the second diamine represented by the formula (V) with the first dianhydride, and the fourth segment structure formed by reacting the second diamine represented by the formula (V) with the second dianhydride, if the structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the unsubstituted aliphatic ring, the unsubstituted aromatic ring, the unsubstituted heterocyclic ring and the unsubstituted fused ring, then at least one of the first soft segment and the second soft segment is any one selected from the hydrophilic segment and the segment including the at least one hydrophilic group, and another is any one selected from a hydrophobic segment and a segment including at least one hydrophobic group; if the structure represented by the formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by the formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the substituted aliphatic ring, the substituted aromatic ring, the substituted heterocyclic ring and the substituted fused ring, then the at least one substituent group in $X_2$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $X_2$ is the hydrophobic group, and at least one of the first soft segment and second soft segment is any one selected from the hydrophilic segment and the segment including the at least one hydrophilic group, and another is any one selected from the hydrophobic segment and the segment including the at least one hydrophobic group, or then at least one of the at least one substituent group in $X_2$, the first soft segment and the second soft segment is any one selected from the hydrophilic segment and the segment including the at least one hydrophilic group, and remaining two are each or a remaining one is any one selected from the hydrophobic segment and the segment including the at least one hydrophobic group; if the structure represented by the formula (II) is selected as the first diamine, and $Y_1$ is any one selected from the substituted aliphatic ring, the substituted aromatic ring, the substituted heterocyclic ring and the substituted fused ring, or if the structure represented by the formula (III) is selected as the first diamine, and $Z_1$ is any one selected from the substituted aliphatic ring, the substituted aromatic ring, the substituted heterocyclic ring and the substituted fused ring, and $X_2$ is any one selected from the unsubstituted aliphatic ring, the unsubstituted aromatic ring, the unsubstituted heterocyclic ring and the unsubstituted fused ring, then the at least one substituent group in $Y_1$ or $Z_1$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and at least one of the first soft segment and the second soft segment is any one selected from the hydrophilic segment and the segment including the at least one hydrophilic group, and another is any one selected from the hydrophobic segment and the segment including the at least one hydrophobic group, or then at least one of the at least one substituent group in $Y_1$ or $Z_1$, the first soft segment and the second soft segment is any one selected from the hydrophilic segment and the segment including the at least one hydrophilic group, and remaining two are each or a remaining one is any one selected from the hydrophobic segment and the segment including the at least one hydrophobic group; and if the structure represented by the formula (II) is selected as the first diamine, and $Y_1$ is any one selected from the substituted aliphatic ring, the substituted aromatic ring, the substituted heterocyclic ring and the substituted fused ring, or if the structure represented by the formula (III) is selected as the first diamine, and $Z_1$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then the at least one substituent group in $Y_1$ or $Z_1$ is the hydrophilic group, and the at least one substituent group in $X_2$ is any one selected from the hydrophilic group and the hydrophobic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the hydrophilic group is selected as the at least one substituent group in $X_2$, and the first soft segment and the second soft segment are each any one independently selected from the hydrophobic segment, the segment including the at least one hydrophobic group, the hydrophilic segment and the segment including the at least one hydrophilic group, or then the hydrophobic group is selected as each of the at least one substituent group in $Y_1$ or $Z_1$ and the at least one substituent group in $X_2$, and at least one of the first soft segment and the second soft segment is any one selected from the hydrophilic segment and the segment including the at least one hydrophilic group, and another is any one selected from the hydrophobic segment and the segment including the at least one hydrophobic group, or then one, two or three of the at least one substituent group in $Y_1$ or $Z_1$, the at least one substituent group in $X_2$, the first soft segment and the second soft segment are each any one selected from the hydrophilic segment and the segment including the at least one hydrophilic group, and remaining three or remaining two are each or a remaining one is any one selected from the hydrophobic segment and the segment including the at least one hydrophobic group.

In some embodiments, the first soft segment is a substituted or unsubstituted alkylene segment having 10 to 20 carbon atoms; a structure represented by the formula (II) is selected as the first diamine, and $Y_1$ is any one selected from the aromatic ring, the heterocyclic ring and the fused ring, in each of which at least one carbon atom is substituted, and at least one substituent group is any one selected from a hydrophilic group and a hydrocarbon group having 1 to 3 carbon atoms and having at least one hydrophilic group; and the second soft segment is any one selected from a hydrophobic segment and a segment including at least one hydrophobic group.

In some embodiments, the second soft segment is a substituted or unsubstituted alkylene segment having 5 to 12 carbon atoms.

In some embodiments, in the first diamine, $Y_1$ is bonded to a para-position of an amino group, and a benzene ring in which a carbon atom is substituted is selected as $Y_1$, and a substituent group is an alcoholic hydroxyl group having 1 to 3 carbon atoms.

In yet another aspect, a liquid crystal aligning agent is provided. The liquid crystal aligning agent includes at least one polymer selected from at least one of a polyamic acid and a group of polyimides obtained by ring closure of the polyamic acid. The polyamic acid includes a fifth segment structure formed by a second dianhydride represented by a following formula (IV) and a second diamine represented by a following formula (V).

(IV)

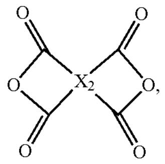

and (V)

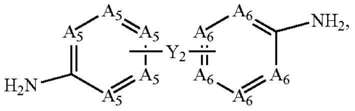

in which $X_2$ in the second dianhydride is any one selected from a substituted or unsubstituted aliphatic ring, a substituted or unsubstituted aromatic ring, a substituted or unsubstituted heterocyclic ring and a substituted or unsubstituted fused ring; $Y_2$ in the second diamine is a second soft segment, and the second soft segment is an amorphous segment; in the second diamine, C is selected as each of a single $A_5$ and a single $A_6$, and the single $A_5$ and the single $A_6$ are both combined with $Y_2$; remaining $A_5$s and remaining $A_6$s are each any one independently selected from CH, CR and N, and neither of a number of Ns in the remaining $A_5$s and a number of Ns the remaining $A_6$s is more than two; R is any one selected from hydrogen and an aliphatic hydrocarbon group; if $X_2$ in the second dianhydride is any one selected from the unsubstituted aliphatic ring, the unsubstituted aromatic ring, the unsubstituted heterocyclic ring and the unsubstituted fused ring, then the second soft segment is any one selected from a hydrophilic segment and a segment including at least one hydrophilic group; if $X_2$ in the second dianhydride is any one selected from the substituted aliphatic ring, the substituted aromatic ring, the substituted heterocyclic ring and the substituted fused ring, then at least one substituent group in $X_2$ is a hydrophilic group, and the second soft segment is any one selected from a hydrophobic segment and a segment including at least one hydrophobic group, or then the at least one substituent group in $X_2$ is a hydrophobic group, and the second soft segment is any one selected from the hydrophilic segment and the segment including the at least one hydrophilic group, or then at least one of the at least one substituent group in $X_2$ and the second soft segment is any one selected from the hydrophobic segment and the segment including the at least one hydrophobic group, and another is any one selected from the hydrophilic segment and the segment including the at least one hydrophilic group.

In yet another aspect, a liquid crystal alignment film is provided. The liquid crystal alignment film is formed by using the above liquid crystal aligning agent.

In some embodiments, hardness of the liquid crystal alignment film is characterized by a depth at which a pricking needle pricks into the liquid crystal alignment film under a preset pressure, and the hardness of the liquid crystal alignment film satisfies that a value thereof is less than or equal to 45 μm under the preset pressure of 150 μN.

In some embodiments, toughness of the liquid crystal alignment film is characterized by a pressure corresponding to an abrupt depth change of a pricking needle in a thickness direction of the liquid crystal alignment film, and a value of the toughness of the liquid crystal alignment film is greater than 390 μN.

In some embodiments, the liquid crystal aligning agent includes a hydrophilic segment and/or a hydrophilic group, a water contact angle of the liquid crystal alignment film is less than or equal to 58 degrees.

In some embodiments, a molar percentage between the first diamine and a second diamine included in the liquid crystal aligning agent is 35%:15%, as a ratio between the first dianhydride and a second dianhydride included in the liquid crystal aligning agent increases, hardness of the liquid crystal alignment film decreases, and toughness of the liquid crystal alignment film increases.

In some embodiments, where a molar percentage between the first dianhydride and a second dianhydride included in the liquid crystal aligning agent is 10%:40%, and $Y_2$ in a second diamine is a hydrophobic segment, as a ratio between the first diamine and the second diamine included in the liquid crystal aligning agent increases, a water contact angle of the liquid crystal alignment film decreases.

In yet another aspect, a display substrate is provided. The display substrate includes a base substrate and a liquid crystal alignment film disposed on the base substrate. The liquid crystal alignment film includes a polyimide obtained after baking the above liquid crystal aligning agent.

BRIEF DESCRIPTION OF THE DRAWINGS

In order to describe technical solutions in the present disclosure more clearly, accompanying drawings to be used in some embodiments of the present disclosure will be introduced briefly below. Obviously, the accompanying drawings to be described below are merely accompanying drawings of some embodiments of the present disclosure, and a person of ordinary skill in the art may obtain other drawings according to these drawings.

In addition, the accompanying drawings to be described below may be regarded as schematic diagrams, but are not limitations on actual sizes of products, actual processes of methods and actual timings of signals to which the embodiments of the present disclosure relate.

DETAILED DESCRIPTION

Figure 1:
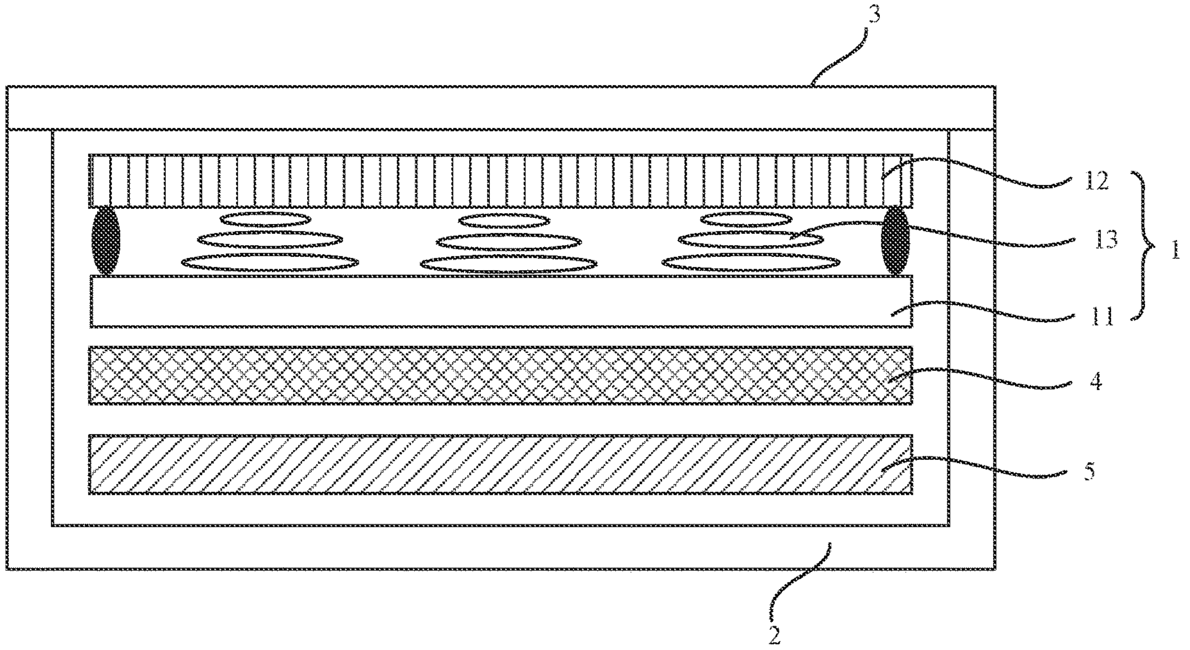
FIG. 1 is a structural diagram of a liquid crystal display device, in accordance with some embodiments.

Technical solutions in some embodiments of the present disclosure will be described clearly and completely below with reference to accompanying drawings. Obviously, the described embodiments are merely some but not all embodiments of the present disclosure. All other embodiments obtained by a person of ordinary skill in the art based on the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to". In the description, the term such as "one embodiment", "some embodiments", "exemplary embodiments", "example", "specific example" or "some examples" is intended to indicate that specific features, structures, materials or characteristics related to the embodiment(s) or example(s) are included in at least one embodiment or example of the present disclosure. Schematic representation of the above term does not necessarily refer to the same embodiment(s) or example(s). In addition, the specific features, structures, materials or characteristics may be included in any one or more embodiments or examples in any suitable manner.

Hereinafter, the terms "first" and "second" are only used for descriptive purposes, and are not to be construed as indicating or implying relative importance or implicitly indicating the number of indicated technical features. Thus, features defined as "first" and "second" may explicitly or implicitly include one or more of the features. In the description of the embodiments of the present disclosure, the term "a/the plurality of" means two or more unless otherwise specified.

The phrase "at least one of A, B and C" has a same meaning as the phrase "at least one of A, B or C", and they both include the following combinations of A, B and C: only A, only B, only C, a combination of A and B, a combination of B and C, and a combination of A, B and C.

The phrase "A and/or B" includes the following three combinations: only A, only B, and a combination of A and B.

As used herein, depending on the context, the term "if" is optionally construed as "when", "in a case where", "in response to determining", or "in response to detecting". Similarly, depending on the context, the phrase "if it is determined . . . " or "if [a stated condition or event] is detected" is optionally construed as "in a case where it is determined . . . ", "in response to determining . . . ", "in a case where [the stated condition or event] is detected", or "in response to detecting [the stated condition or event]".

In the description of some embodiments, the terms "coupled" and "connected" and derivatives thereof may be used. For example, the term "connected" may be used in the description of some embodiments to indicate that two or more components are in direct physical or electrical contact with each other. For another example, the term "coupled" may be used in the description of some embodiments to indicate that two or more components are in direct physical or electrical contact. However, the term "coupled" or "communicatively coupled" may also mean that two or more components are not in direct contact with each other, but still cooperate or interact with each other. The embodiments disclosed herein are not necessarily limited to the contents herein.

Exemplary embodiments are described herein with reference to sectional views and/or plan views as idealized exemplary accompanying drawings. In the accompanying drawings, thicknesses of layers and areas of regions are enlarged for clarity. Thus, variations in shapes with respect to the accompanying drawings due to, for example, manufacturing technologies and/or tolerances may be envisaged. Therefore, the exemplary embodiments should not be construed as being limited to the shapes of the regions shown herein, but including deviations in the shapes due to, for example, manufacturing. For example, an etched region shown in a rectangular shape generally has a curved feature. Thus, the regions shown in the accompanying drawings are schematic in nature, and their shapes are not intended to show actual shapes of the regions in a device, and are not intended to limit the scope of the exemplary embodiments.

Some embodiments of the present disclosure provide a liquid crystal display (LCD) device. The liquid crystal display device may be a liquid crystal display panel, or may include the liquid crystal display panel, such as a mobile phone, a tablet computer, a notebook computer, a personal digital assistant (PDA), or an in-vehicle computer.

As shown in FIG. 1, in a case where the liquid crystal display device includes the liquid crystal display panel 1, the liquid crystal display device may further include a frame 2, a cover glass 3, a backlight module 4, a circuit board 5, a camera, and other accessories. The backlight module 4 is configured to provide backlight to the liquid crystal display panel 1. The circuit board 5 is coupled to the liquid crystal display panel 1, and is configured to provide an electrical signal to the liquid crystal display panel 1, so as to control the liquid crystal display panel 1 to display an image.

As shown in FIG. 1, a longitudinal section of the frame 2 may be U-shaped, and the liquid crystal display panel 1, the backlight module 4, the circuit board 5 and other electronic accessories are disposed in the frame 2. The backlight module 4 is disposed under the liquid crystal display panel 1. The circuit board 5 is disposed under the backlight module 4. The cover glass 2 is located on a side of the liquid crystal display panel 1 away from the backlight module 4.

Figure 2A:
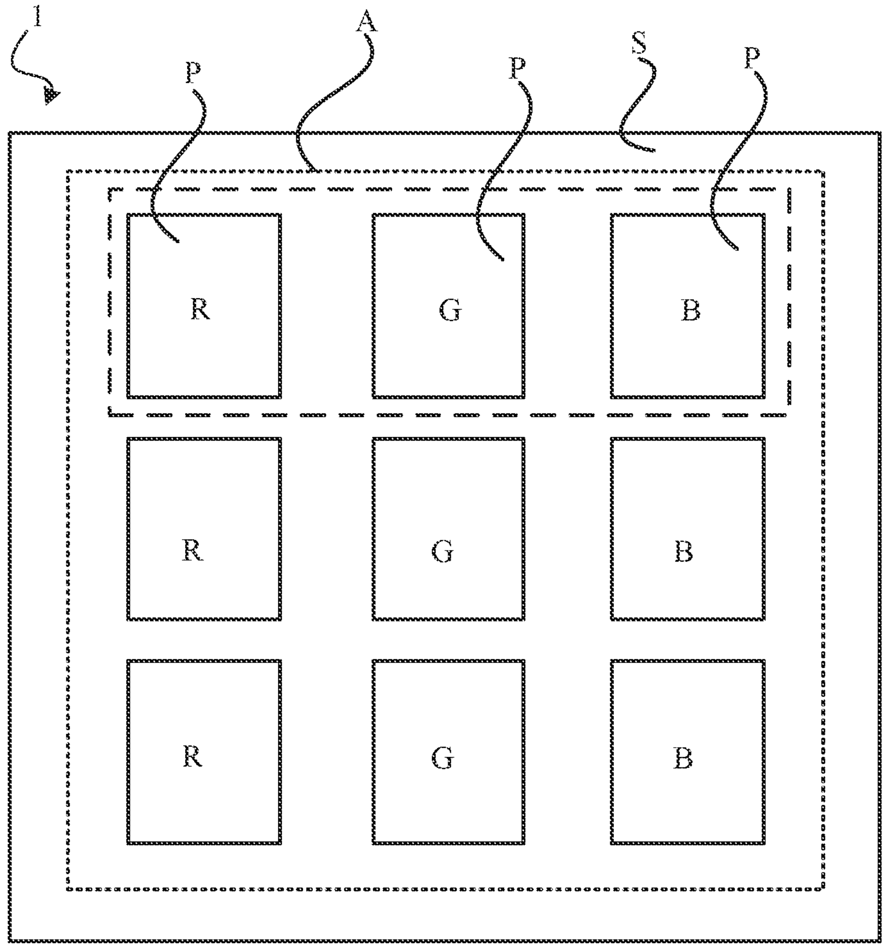
FIG. 2A is a top view of a display panel, in accordance with some embodiments.

Based on the above structure of the liquid crystal display device, some embodiments of the present disclosure provide a liquid crystal display panel 1. As shown in FIG. 2A, the liquid crystal display panel 1 includes an active area (abbreviated as AA) A and a peripheral area S arranged around the active area A. The active area A includes a plurality of pixel areas (the dashed box in the figure indicates a pixel). Each pixel area includes at least three sub-pixel areas P, which are a red sub-pixel area R, a green sub-pixel area G and a blue sub-pixel area B, respectively. The peripheral area S is an area in the liquid crystal display panel except the active area A, and is used for wiring. In addition, a gate driver circuit may further be disposed in the peripheral area S.

Figure 2B:
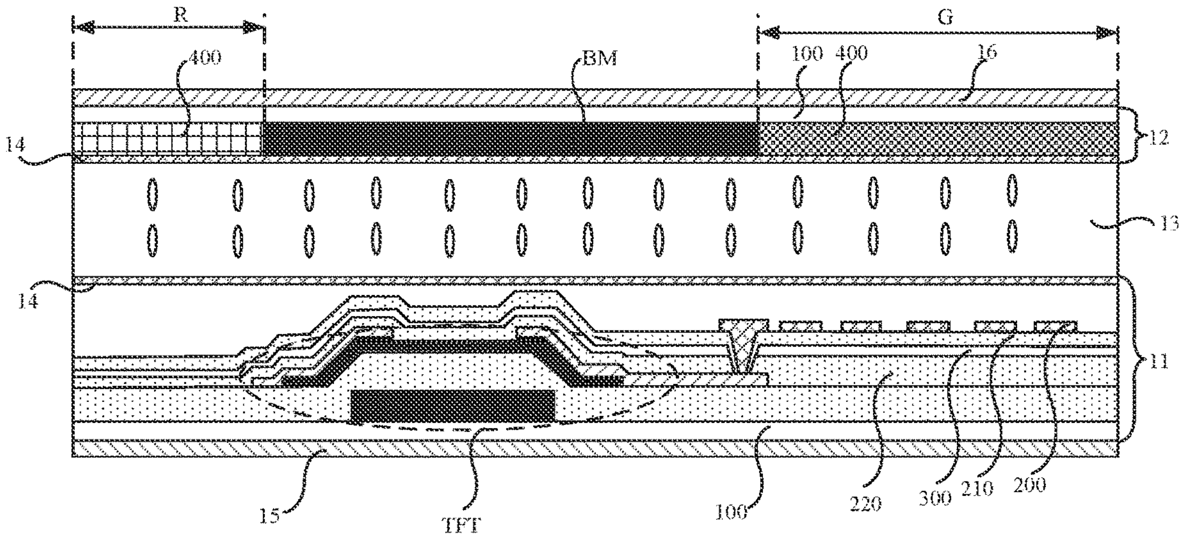
FIG. 2B is a sectional view of a liquid crystal display device, in accordance with some embodiments.

In some embodiments, as shown in FIG. 2B, the liquid crystal display panel 1 includes a first substrate 11 and a second substrate 12 that are disposed opposite to each other, and a liquid crystal layer 13 disposed between the first substrate 11 and the second substrate 12. The first substrate 11 and the second substrate 12 are respectively an array substrate and an opposite substrate (the array substrate and the opposite substrate may each be referred to as a display substrate). The array substrate and the opposite substrate are assembled together through a frame sealant, so that the liquid crystal layer 13 is confined in a region enclosed by the frame sealant.

As shown in FIG. 2B, the display substrate includes a base substrate 100, and a liquid crystal alignment film 14 disposed on the base substrate 100. The liquid crystal alignment film 14 is configured to define an initial alignment of liquid crystal molecules in the liquid crystal layer 13 (i.e., an alignment of the liquid crystal molecules when no power is supplied to the liquid crystal display panel 1).

Here, as shown in FIG. 2B, in a case where the display substrate is the array substrate, in addition to the base substrate 100 and the liquid crystal alignment film 14 disposed on the base substrate 100, the display substrate further includes a thin film transistor (TFT) disposed in each sub-pixel area and located on the base substrate 100, and a pixel electrode 200 electrically connected to a drain or a source of the TFT. On this basis, the display substrate may further include a common electrode 300 disposed in each sub-pixel area. As shown in FIG. 2B, the common electrode 300 and the pixel electrode 200 are separated by a first insulating layer 210. In addition, in a case where the common electrode 300 is located between the TFT and the pixel electrode 200, a second insulating layer 220 may be provided between the TFT and the common electrode 300. In this case, the pixel electrode 200 is electrically connected to the drain or the source of the TFT through a channel in the first insulating layer 210, the common electrode 300 and the second insulating layer 220. The first insulating layer 210 and the second insulating layer 220 are each integrally laid in the active area A, and a part thereof in a desired area may be removed from the area by patterning or the like to form the channel (which may also be referred to as a via hole).

As shown in FIG. 2B, in a case where the display substrate is the opposite substrate, in addition to the base substrate 100 and the liquid crystal alignment film 14 disposed on the base substrate 100, the display substrate may further include a color filter layer 400 disposed on a surface of the base substrate 100 facing the liquid crystal layer 13. In this case, the opposite substrate 12 is referred to as a color filter substrate. The color filter layer 400 includes red filter patterns each located in the red sub-pixel area R, green filter patterns each located in the green sub-pixel area G, and blue filter patterns each located in the blue sub-pixel area.

In order to avoid crosstalk between adjacent sub-pixels, the display substrate (which is the opposite substrate here) may further include a black matrix (BM). The black matrix includes a plurality of first light-shielding strips parallel to one another and a plurality of second light-shielding strips parallel to one another. The plurality of first light-shielding strips and the plurality of second light-shielding strips enclose a plurality of spaces, and each space is a sub-pixel area.

It will be noted that, the liquid crystal display panel 1 above is described by taking an example in which the common electrode 300 is disposed on the base substrate of the array substrate. In this case, the liquid crystal display panel 1 is an advanced-super dimensional switching (AD-SDS) display panel. One of the pixel electrode 200 and the common electrode 300 has slits, and positions of the two may be changed up and down, but one of the pixel electrode 200 and the common electrode 300 that is connected to the drain or the source of the thin film transistor is the pixel electrode 300. However, the present disclosure is not limited thereto. For example, the liquid crystal display panel 1 may be a fringe field switching (FFS) display panel or an in-plane switching (IPS) display panel. In addition, the common electrode 300 may be disposed on the base substrate of the opposite substrate, in which case the liquid crystal display panel 1 is a twist nematic (TN) display panel or the like.

Based on the above structure, since the liquid crystal molecules are anisotropic when they are in a liquid crystal state, photoelectric effects of the liquid crystal molecules are different due to different rotation directions thereof. That is to say, photoelectric properties of the liquid crystal molecules, such as a dielectric coefficient (a property of the liquid crystal molecule rotating due to action of an electric field) and a refraction coefficient (a property of the liquid crystal molecule affecting a polarization state of light when the light passes through the liquid crystal molecule), are all anisotropic. Therefore, the rotation of the liquid crystal molecules is controlled by using these properties of liquid crystal itself and by using voltages appropriately, thereby affecting the polarization state of the light to generate different gray scales, and in turn achieving display.

However, the display cannot be achieved simply by relying on the liquid crystal molecules, and polarizers and the liquid crystal alignment film 14 disposed on the base substrate 100 are also required.

As shown in FIG. 2B, the liquid crystal display panel 1 further includes a lower polarizer 15 (which may also be referred to as a first polarizer) disposed on a side of the first substrate 11 facing away from the liquid crystal layer 13, and an upper polarizer 16 (which may also be referred to as a second polarizer) disposed on a side of the second substrate 12 facing away from the liquid crystal layer 13.

A function of the polarizer is to allow polarized light in a direction parallel to a polarization axis (i.e., a transmission direction) to pass. A transmission direction of the lower polarizer 15 is perpendicular or parallel to a transmission direction of the upper polarizer 16. For example, a polarization state of linearly polarized light emitted from the lower polarizer 15 is changed after the linearly polarized light passes through the liquid crystal layer 13 controlled by an electric field, and only a light component parallel to the transmission direction of the upper polarizer 16 can pass through the upper polarizer 16, thereby achieving display with different gray scales. In this process, the liquid crystal alignment film 14 functions to define the initial alignment of the liquid crystal molecules.

Figure 3:
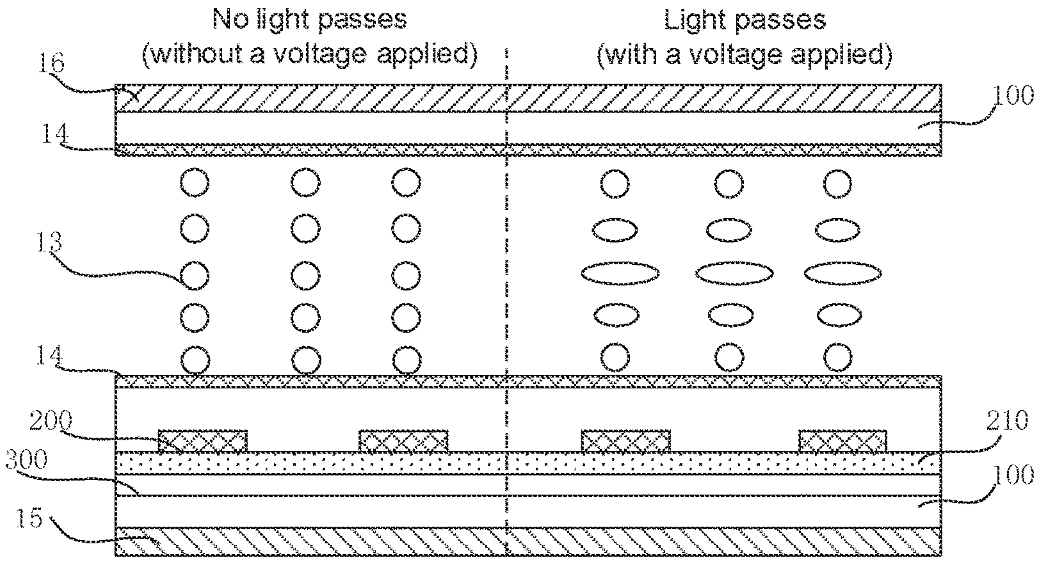
FIG. 3 is a diagram showing a comparison between a structure of a fringe field switching (FFS)-type liquid crystal display device when no voltage is applied thereto and a structure of the FFS-type liquid crystal display device when a voltage is applied thereto, in accordance with some embodiments.

In some embodiments, considering the AD-SDS liquid crystal display panel as an example, as shown in FIG. 3, the transmission direction of the upper polarizer 16 is perpendicular to the transmission direction of the lower polarizer 15, and alignment directions of the liquid crystal alignment films 14 disposed on the two base substrate 100 are parallel to each other. When no voltage is applied to a sub-pixel, the liquid crystal molecules are arranged in a same direction, and the sub-pixel is in a black state. After applying a voltage to a pixel electrode 200 and a common electrode 300 of the sub-pixel, a fringe electric field is generated in the liquid crystal layer 13. The liquid crystal molecules may rotate in a plane parallel to the base substrate 100 due to action of the fringe electric field, so that optical axes of the liquid crystal molecules deviate from a polarization axis (a transmission axis) of the lower polarizer 15, and a polarization phenomenon occurs. This part of polarized light can pass through the upper polarizer 16, so that the sub-pixel is in a white display state.

Figure 4A:
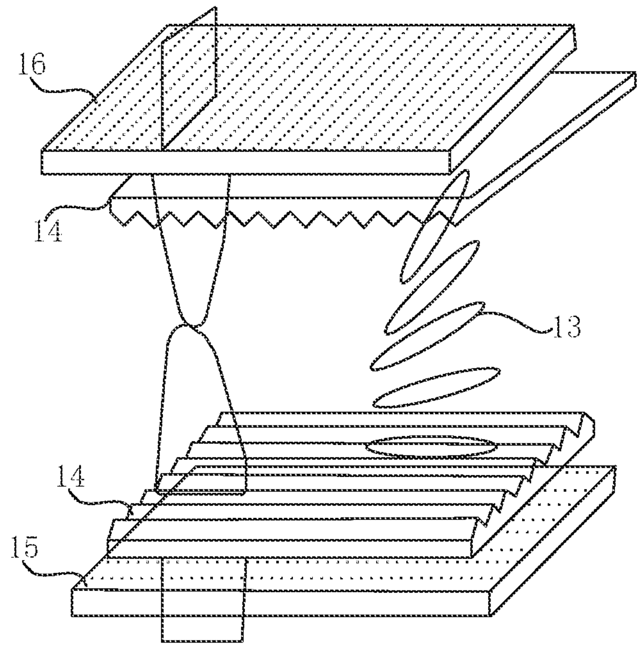
FIG. 4A is structural diagram of a twist nematic (TN)-type liquid crystal display device when no voltage is applied thereto, in accordance with some embodiments.
Figure 4B:
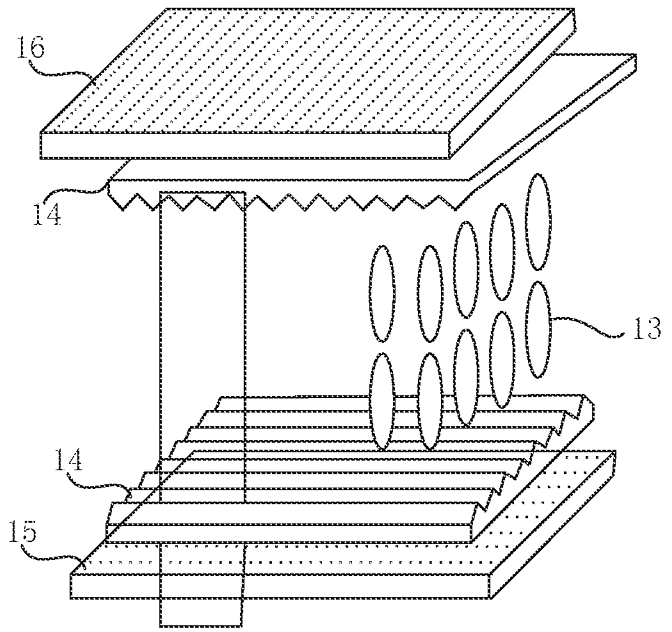
FIG. 4B is structural diagram of the TN-type liquid crystal display device when a voltage is applied thereto, in accordance with some embodiments.

In some other embodiments, considering the TN liquid crystal display panel as an example, as shown in FIGS. 4A and 4B, the alignment directions of the two liquid crystal alignment films 14 disposed on the two base substrates are perpendicular to each other, and the liquid crystal molecules form a twisted alignment structure with a twist angle of 90 degrees. Considering a normally white mode in which the upper polarizer 16 and the lower polarizer 15 are perpendicular to each other as an example, when no voltage is applied, the TN liquid crystal display panel is in a white display state; after a voltage is applied, the liquid crystal molecules are arranged vertically, and after the incident linearly polarized light passes through the liquid crystal layer 13, the polarized light cannot pass through the upper polarizer 16, and thus the TN liquid crystal display panel is in a black display state.

It can be seen from the above examples that, the liquid crystal display device cannot work normally if the liquid crystal alignment film 14 is not provided. That is, if the liquid crystal alignment film 14 cannot function to define the initial alignment of the liquid crystal molecules, the liquid crystal molecules will be arranged irregularly when no voltage is applied, thereby causing scattering of light and a phenomenon of light leakage.

In light of this, some embodiments of the present disclosure provide a liquid crystal alignment film. The liquid crystal alignment film is made of a liquid crystal aligning agent, and includes a polyimide obtained after baking the liquid crystal aligning agent.

After the liquid crystal alignment film is rubbed for alignment, the liquid crystal alignment film 14 may be obtained.

Of course, a person skilled in the art can understand that, the liquid crystal alignment film provided by the present disclosure is also applicable to optical alignment in a case where the liquid crystal alignment film may be aligned by an optical action.

Raw materials of the liquid crystal alignment film used in engineering are mainly divided into a polyamic acid and a soluble polyimide. The polyamic acid may be formed by mixing and dissolving a dianhydride and a diamine in a specific solvent, and the polyimide is formed by dehydrating the polyamic acid.

Therefore, in practical production, the raw materials of the liquid crystal alignment film, such as the dianhydride and the diamine, may be first mixed in a solvent, and are stirred under protection of nitrogen, so that a polymerization reaction occurs to generate the polyamic acid. Then, the polyamic acid is purified and then diluted with a solvent in a certain proportion, thereby obtaining the liquid crystal aligning agent. Then, the liquid crystal aligning agent is applied on the base substrate (here, the base substrate may be a base substrate on which the TFT, the pixel electrode and the common electrode have been formed, or a base substrate on which the color filter layer and the black matrix have been formed). Next, the liquid crystal aligning agent is cured through a pre-curing process (at a temperature of 125° C. to 135° C., and within a time of 110 s to 150 s) and a main curing process (at a temperature of 210° C. to 240° C., and within a time of 1100 s to 1500 s). Finally, the polyamic acid is dehydrated by baking to generate the polyimide.

The liquid crystal aligning agent may be applied on the base substrate by means of letterpress printing or ink jetting. The letterpress printing has advantages of accurate pattern selection and uniform printed surface. The ink jetting is applicable to fabrication of large-size display panels, and compared to the letterpress printing, the ink jetting uses less liquid crystal aligning agent, and is more efficient and less costly.

Embodiment 1 of the present disclosure provides a liquid crystal aligning agent including at least one polymer selected from at least one of a polyamic acid and a group of polyimides obtained by ring closure of the polyamic acid. The polyamic acid includes a first segment structure formed by a first dianhydride represented by the following formula (I) and a first diamine represented by the following formula (II) or formula (III).

(I)

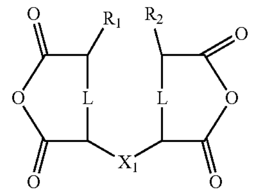

(II)

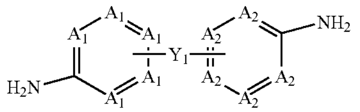

(III)

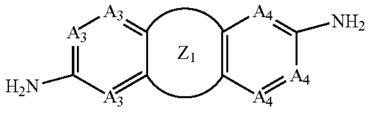

Where $X_1$ in the first dianhydride is a first soft segment, and the first soft segment is an amorphous segment; and L is any one selected from a single bond, a double bond and a divalent or trivalent hydrocarbon group having 1 to 3 carbon atoms.

In the first diamine represented by formula (II), $Y_1$ is any one selected from the single bond, O, NH, S, one or more unsaturated double bonds, a substituted or unsubstituted aliphatic ring, a substituted or unsubstituted aromatic ring, a substituted or unsubstituted heterocyclic ring and a substituted or unsubstituted fused ring; C is selected as each of a single $A_1$ and a single $A_2$, and the single $A_1$ and the single $A_2$ are both combined with $Y_1$; remaining $A_1$s and remaining $A_2$s are each any one independently selected from CH, CR and N, and neither of the number of Ns in the remaining $A_1$s and the number of Ns in the remaining $A_2$s is more than two.

In the first diamine represented by formula (III), $Z_1$ is any one selected from the substituted or unsubstituted aliphatic ring, substituted or unsubstituted aromatic ring, substituted or unsubstituted heterocyclic ring and substituted or unsubstituted fused ring; $A_3$s and $A_4$s are each any one independently selected from CH, CR and N, and neither of the number of Ns in the $A_3$s and the number of Ns in the $A_4$s is more than two; $R_1$, $R_2$ and R are each any one independently selected from hydrogen and an aliphatic hydrocarbon group.

The divalent hydrocarbon group having 1 to 3 carbon atoms may be: $—CH_2—$, $—CH_2—CH_2—$, $—CH_2—CH_2—CH_2—$, $—CH═CH—$, $—CH_2—CH═CH—$, or $—CH═CH—$. The trivalent hydrocarbon group having 1 to 3 carbon atoms may be: $═CH—$, $═CH—CH_2—$, $═CH—CH_2—CH_2—$, or $═CH—CH═CH—$.

In a case where a single bond is selected as L, a structure of formula (I) may be shown as the following formula (i):

(i)

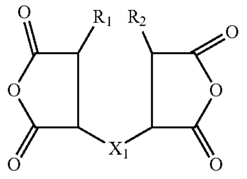

In a case where a double bond is selected as L, the structure of formula (I) may be shown as the following formula (ii):

(ii)

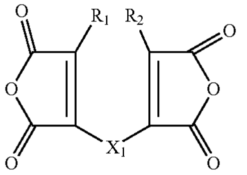

In a case where a divalent hydrocarbon group having 1 to 3 carbon atoms is selected as L, and the divalent hydrocarbon group having 1 to 3 carbon atoms is $—CH_2—$, the structure of formula (I) may be shown as the following formula (iii):

(iii)

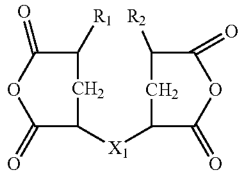

In a case where a trivalent hydrocarbon group having 1 to 3 carbon atoms is selected as L, and the trivalent hydrocarbon group having 1 to 3 carbon atoms is $═CH—$, the structural formula of formula (I) may be shown as the following formula (iv):

(iv)

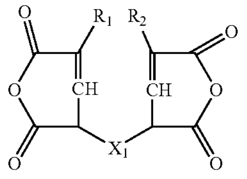

In polymers, there are different molecular segments in some block copolymers. Some molecular segments are composed of aromatic hydrocarbons and have great rigidity, and thus are referred to as hard segments; some other molecular segments are composed of aliphatic hydrocarbons and have great flexibility, and thus are referred to as soft segments.

It can be seen that soft segments are described relative to hard segments.

In this embodiment, in addition to the aromatic hydrocarbon in the block copolymers, the hard segment may further include a polycyclic ring, a fused ring, and a conjugated system having an aromatic ring, such as the structure of the first diamine shown above. In addition to the aliphatic hydrocarbon, the soft segment may further include a segment composed of a carbon-oxygen bond, a carbon-nitrogen bond, a carbon-silicon bond, and a silicon-oxygen bond.

The polymers may be classified into crystalline polymers and amorphous (non-crystalline) polymers according to regularity of their molecular arrangement in space. Correspondingly, in the polymers, the segments may be classified into crystalline segments and amorphous segments according to regularity of arrangement of the molecular segments in space. In a case where molecules in a segment are arranged regularly and orderly, the segment is referred to as a crystalline segment. In a case where molecules in a segment are arranged irregularly and disorderly, the segment is referred to as an amorphous segment.

In general, an amorphous segment is often obtained in a case where molecules thereof have a branched structure, a cross-linked structure, an atactic structure, a random copolymerization structure, a structure with large side groups or the like. Strictly speaking, the amorphous segment refers to a segment that does not crystallize under any conditions, and a segment with very low crystallinity is often included in practice.

The atactic structure means that configuration with substituent groups on two sides of a plane or at a chiral center is irregular. The random copolymerization structure is formed by connecting two (or more than two) monomeric units arranged irregularly. Sequence length distributions of the two monomeric units are both irregular.

In this embodiment, the first soft segment is an amorphous segment, and thus there are two possible cases. In a first case, the first dianhydride has an asymmetrical structure. In a second case, the first soft segment includes asymmetrical branches.

Symmetry of a molecule means that the molecule often has a certain symmetry since it has several identical atoms or groups. If the molecule is subjected to a certain symmetry operation (the symmetry operation has its symmetry element, and the symmetry of the molecule may be divided into five symmetry elements: a rotation axis, a symmetry plane, a symmetry center, a rotation reflection axis and an identity element), and the molecule cannot be distinguished from an original molecule that is not subjected to the operation, it means that the molecule has the symmetry. In this case, a structure of the molecule is a symmetrical structure, and conversely, the structure of the molecule is an asymmetrical structure.

As for the first dianhydride, considering an example in which a double bond is selected as L, since the first dianhydride has two succinic anhydrides, and $X_1$ is connected between the two succinic anhydrides, if $R_1$ and $R_2$ are located on a same side of $X_1$, the first dianhydride is cis-dianhydride, and conversely, the first dianhydride is trans-dianhydride. In a case where the first dianhydride is cis-dianhydride, the first dianhydride is applicable to a determination criterion that the symmetry element is the symmetry plane. In this case, if the first dianhydride is mirror-symmetrical, the first dianhydride has a symmetrical structure, and conversely, the first dianhydride has an asymmetrical structure. Therefore, in this case, in order to make the first dianhydride have the asymmetrical structure, for example, the substituents $R_1$ and $R_2$ are different. In this case, the first soft segment may include asymmetrical branches, or may not include asymmetrical branches, which is the first case. In a case where the first dianhydride is trans-dianhydride, the first dianhydride is applicable to a determination criterion that the symmetry element is the symmetry center. In this case, if the first dianhydride is centrosymmetric, the first dianhydride has a symmetrical structure, and conversely, the first dianhydride has an asymmetrical structure. Therefore, in this case, in order to make the first dianhydride have the asymmetrical structure, for example, the substituents $R_1$ and $R_2$ are different. In this case, similar to the case where the first dianhydride is cis-dianhydride, the first soft segment may include asymmetrical branches, or may not include asymmetrical branches, which is the first case.

In the second case where the first soft segment includes asymmetrical branches, there are two possible cases depending on whether the first dianhydride is cis-dianhydride or trans-dianhydride. In a first case, the first dianhydride is cis-dianhydride, and then a criterion for determining whether the branches in the first soft segment are asymmetrical branches is same as a criterion for determining whether the first dianhydride has a symmetrical structure, and both are determined by taking the symmetry plane as the symmetry element. In a second case, the first dianhydride is trans-dianhydride, and then the criterion for determining whether the branches in the first soft segment are asymmetrical branches is same as the criterion for determining whether the first dianhydride has a symmetrical structure, and both are determined by taking the symmetry center as the symmetry element.

It can be seen from the above that, the polyamic acid may have a structure with the first segment structure as a repeating unit. Depending on different structures of the first diamine, the polyamic acid has two possible structures, in which a first structure is represented by the following formula (1), and a second structure is represented by the following formula (2).

(1)

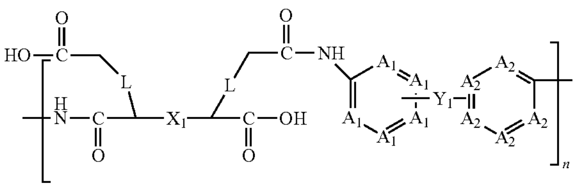

(2)

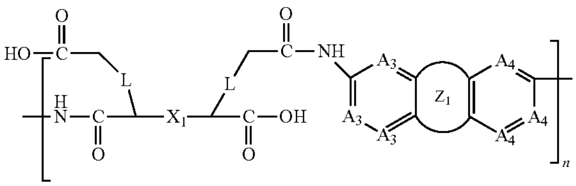

It can be seen from the above structures that, the polyamic acid is formed by alternately arranging amorphous soft segments and amorphous hard segments. Therefore, by reasonably proportioning the soft segments and the hard segments in the molecular structure, the polyamic acid may be endowed with special properties. For example, toughness of the polyamic acid may be improved while the polyamic acid has good rigidity. As for a polyimide in the related art, although it has good hardness (which may be up to 3 H to 4 H), it is easy to generate debris and damage a rubbing cloth due to the excessively high hardness during rubbing alignment, causing falling off of components of the rubbing cloth. Compared with the polyimide in the related art, the polyamic acid has good toughness, and thus when the rubbing cloth is used for rubbing during the rubbing alignment, a product (polyimide) obtained after baking the polyamic acid has good ductility, and may well buffer external force generated by the rubbing cloth. Consequently, the polyimide itself is not easy to generate debris, and the polyimide is not easy to damage the rubbing cloth, and in turn, the defect of debris may be effectively avoided.

Based on the above structures, in some embodiments, if the structure represented by formula (II) is selected as the first diamine, and $Y_1$ is any one selected from a single bond, O, NH, S, one or more unsaturated double bonds, an unsubstituted aliphatic ring, an unsubstituted aromatic ring, an unsubstituted heterocyclic ring and an unsubstituted fused ring, or if the structure represented by formula (III) is selected as the first diamine, and $Z_1$ is any one selected from the unsubstituted aliphatic ring, the unsubstituted aromatic ring, the unsubstituted heterocyclic ring and the unsubstituted fused ring, then the first soft segment is any one selected from a hydrophilic segment and a segment including at least one hydrophilic group.

If the structure represented by formula (II) is selected as the first diamine, and $Y_1$ is any one selected from the substituted aliphatic ring, the substituted aromatic ring, the substituted heterocyclic ring and the substituted fused ring, then at least one substituent group in $Y_1$ is any one selected from a hydrophobic group and a hydrophilic group, and the first soft segment is any one selected from the hydrophilic segment and the segment including the at least one hydrophilic group, or then the hydrophilic group is selected as the at least one substituent group in $Y_1$, and the first soft segment is any one selected from the hydrophobic segment, the segment including the at least one hydrophobic group, the hydrophilic segment and the segment including the at least one hydrophilic group, or then one of the at least one substituent group in $Y_1$ and the first soft segment is any one selected from the hydrophilic segment and the segment including the at least one hydrophilic group, and the other one is any one selected from the hydrophobic segment and the segment including at least one hydrophobic group.

If the structure represented by formula (III) is selected as the first diamine, and $Z_1$ is any one selected from the substituted aliphatic ring, the substituted aromatic ring, the substituted heterocyclic ring and the substituted fused ring, then at least one substituent group in $Z_1$ is any one selected from the hydrophobic group and the hydrophilic group, and the first soft segment is any one selected from the hydrophilic segment and the segment including the at least one hydrophilic group, or then the hydrophilic group is selected as the at least one substituent group in $Z_1$, and the first soft segment is any one selected from the hydrophobic segment, the segment including the at least one hydrophobic group, the hydrophilic segment and the segment including the at least one hydrophilic group, or then one of the at least one substituent group in $Z_1$ and the first soft segment is any one selected from the hydrophilic segment and the segment including the at least one hydrophilic group, and the other one is any one selected from the hydrophobic segment and the segment including the at least one hydrophobic group.

In amphiphilic polymers, there are a hydrophilic segment and a hydrophobic segment in a same molecular chain, and the hydrophobic segment is described relative to the hydrophilic segment. The hydrophilic segment may include a polyethylene glycol segment, a polyvinyl ether segment, a polyvinyl alcohol segment, a polyethylenimine segment, a polyvinylpyrrolidone segment, or a polyvinyl amide segment. The hydrophobic segment may include a polypropylene oxide segment, a polysiloxane segment, a saturated aliphatic hydrocarbon segment (e.g., a polystyrene segment, a polyethylene segment, a polypropylene segment, a polymethyl methacrylate segment, a polymethyl acrylate segment, or a polybutyl acrylate segment), or an unsaturated aliphatic hydrocarbon segment (e.g., a polybutadiene segment).

The hydrophilic group, also known as an oleophobic group, has an atomic group that is soluble in water or easily affinitive to water. The hydrophilic group is likely to attract water molecules or dissolve in water, and a surface of a solid formed by such molecules is easily wetted by water. The hydrophilic group includes a carboxyl group, a sulfonic group, a phosphate group, an amino group, a quaternary ammonium group, or an ether group, a hydroxyl group, a carboxylic ester or a block polyether which is composed of oxygen-containing groups.

The hydrophobic group, also known as a lipophilic group, has no affinity for water, and is a group that is insoluble or has very low solubility in water. The hydrophobic group includes a hydrocarbon group or an ester group. The hydrocarbon group may be a saturated aliphatic hydrocarbon, or an unsaturated aliphatic hydrocarbon including a double bond, or a hydrocarbon group including an aromatic group, an ester group, an ether group, an amine group, an amide group, or the like.

In these embodiments, in a case where the structure represented by formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or in a case where the structure represented by formula (III) is selected as the first diamine, and $Z_1$ is any one selected from the unsubstituted aliphatic ring, the unsubstituted aromatic ring, the unsubstituted heterocyclic ring and the unsubstituted fused ring, the first diamine is a hydrophobic segment. Therefore, hydrophilicity or hydrophobicity of the polyamic acid may be adjusted by setting the first soft segment as the hydrophilic segment or introducing the hydrophilic group into the first soft segment, and by reasonably proportioning hydrophobic segments and hydrophilic segments or hydrophilic groups. Alternatively, in a case where the structure represented by formula (II) is selected as the first diamine, and $Y_1$ is any one selected from the substituted aliphatic ring, the substituted aromatic ring, the substituted heterocyclic ring and the substituted the substituted fused ring, or in a case where the structure represented by formula (III) is selected as the first diamine, and $Z_1$ is any one selected from the substituted aliphatic ring, the substituted aromatic ring, the substituted heterocyclic ring and the substituted fused ring, the hydrophilicity or hydrophobicity of the polyamic acid may also be adjusted by adjusting hydrophilicity or hydrophobicity of the substituent group and hydrophilicity or hydrophobicity of the first soft segment, and by reasonably proportioning hydrophilic groups and hydrophobic groups in the substituent group and the first soft segment.

As for a hydrophobic polyamic acid, a contact angle of water on a surface of the hydrophobic polyamic acid is large, a wetting effect is poor, and a water film is not easily formed. Debris is adsorbed on the surface of the hydrophobic polyamic acid, and is not easy to enter the water; and during drying with an air knife, the water on the surface of the polyamic acid is blown out quickly, resulting in a poor cleaning effect and a low removal rate of the debris. Conversely, as for a hydrophilic polyamic acid, a contact angle of water on a surface of the hydrophilic polyamic acid is small, a wetting effect is good, and a uniform water film is easily formed. Debris is easy to enter the water, and is finally blown away by the air knife. However, if hydrophilicity of the hydrophilic polyamic acid is too strong, it may easily adsorb moisture in the environment, causing pollution of dust particles in the environment, thereby generating debris such as foreign matters in the environment.

Therefore, in these embodiments, by adjusting the hydrophilicity or hydrophobicity of the polyamic acid, the polyamic acid may have an appropriate hydrophilicity or hydrophobicity. In this way, after the rubbing alignment is completed and before a LCD cell is formed, by cleaning the surface of the liquid crystal alignment film having the polyamic acid, the debris and impurities (e.g., lint of the rubbing cloth) generated during the rubbing alignment may be effectively removed. This may avoid the defect of debris, as compared with the related art in which the surface of the liquid crystal alignment film cannot be effectively cleaned before the cell is formed, and thus the debris and impurities remain in the cell, causing the defect of debris (e.g., large debris may directly lead to a low yield, and small debris may lead to light leakage in the black state and reduce contrast of the product).

In some other embodiments, the first soft segment is any one of a hydrophobic segment and a segment including at least one hydrophobic group; the structure represented by formula (II) is selected as the first diamine, and $Y_1$ is any one selected from an aromatic ring, a heterocyclic ring and a fused ring, in each of which at least one carbon atom is substituted, and at least one substituent group is any one selected from a hydrophilic group, and a hydrocarbon group having 1 to 3 carbon atoms and having at least one hydrophilic group.

In these embodiments, since $Y_1$ is any one selected from the aromatic ring, the heterocyclic ring and the fused ring, in a case where a hydrophilic group is selected as the at least one substituent group, the hydrophilic group is directly bonded to the ring of $Y_1$. Furthermore, in a case where the hydrophilic group is a hydroxyl group, the substituent group is a phenolic hydroxyl group. In a case where a hydrocarbon group having 1 to 3 carbon atoms and having at least one hydrophilic group is selected as the at least one substituent group, the hydrophilic group is bonded to the hydrocarbon group. Therefore, in a case where the hydrophilic group is a hydroxyl group, the substituent group is an alcoholic hydroxyl group.

In some other embodiments, in the first diamine, $Y_1$ is bonded to a para-position of an amino group, and a benzene ring in which a carbon atom is substituted is selected as $Y_1$, and a substituent group is an alcoholic hydroxyl group having 1 to 3 carbon atoms.

That is, this is a case where the hydrophilic group is an alcoholic hydroxyl group. In addition, in these embodiments, since $Y_1$ is bonded to the para-position of the amino group, in a case where the $A_1$s and the $A_2$s are each any one independently selected from CH and CR, the first diamine is terphenyl.

In yet some other embodiments, the first soft segment is a substituted or unsubstituted alkylene segment having 10 to 20 carbon atoms.

In these embodiments, in a case where the first soft segment is the unsubstituted alkylene segment having 10 to 20 carbon atoms, since the first soft segment is the amorphous segment, the first dianhydride has an asymmetrical structure. In this case, $R_1$ and $R_2$ are different, and as for a specific determination criterion, reference may be made to the above description that the first dianhydride has the asymmetrical structure. In a case where the first soft segment is the substituted alkylene segment having 10 to 20 carbon atoms, since the first soft segment is the amorphous segment, the first dianhydride has an asymmetrical structure. That is, in a case where the substituent group forms symmetrical branches, $R_1$ and $R_2$ are different. Alternatively, the first soft segment includes asymmetrical branches. In this case, $R_1$ and $R_2$ may be same, and it may also be possible to achieve that the first soft segment is the amorphous segment. As for a specific determination criterion, reference may be made to the above description that the first dianhydride has an asymmetrical structure, or the description that the first soft segment includes an asymmetrical structure.

Embodiment 2 of the present disclosure provides a liquid crystal aligning agent including at least one polymer selected from at least one of a polyamic acid and a group of polyimides obtained by ring closure of the polyamic acid. In addition to the first segment structure formed by the first dianhydride represented by the above formula (I) and the first diamine represented by the above formula (II) or formula (III), the polyamic acid further includes a second segment structure formed by a second dianhydride represented by the following formula (IV) and the first diamine represented by the above formula (II) or formula (III).

(IV)

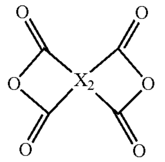

Where $X_2$ in the second dianhydride is any one selected from an aliphatic ring, an aromatic ring, a heterocyclic ring and a fused ring.

In this embodiment, since $X_2$ in the second dianhydride is any one selected from the aliphatic ring, the aromatic ring, the heterocyclic ring and the fused ring, the second dianhydride has a planar molecular structure and a high rigidity. The second dianhydride is used as a hard segment in the second segment structure formed by reacting the second dianhydride with the first diamine. Considering an example in which the anhydride and the diamine are polymerized in a molar ratio of 1:1, a ratio of a total molar amount of the first dianhydride and the second dianhydride to a molar amount of the first diamine may be close to 1:1 during mixing. For example, the ratio may be in a range from 9:11 to 11:9, inclusive. In this case, the first dianhydride and the second dianhydride are both polymerized with the first diamine, and by adjusting a ratio of the first dianhydride to the second dianhydride, a ratio of the first segment structure formed by the first dianhydride and the first diamine to the second segment structure formed by the second dianhydride and the first diamine (i.e., a ratio between segment structures (which may be represented by the following formula (3) or formula (4) depending on different structures of the first diamine) in the polyamic acid, which are obtained by polymerizing the first dianhydride and the second dianhydride with a same first diamine) may be adjusted.

(3)

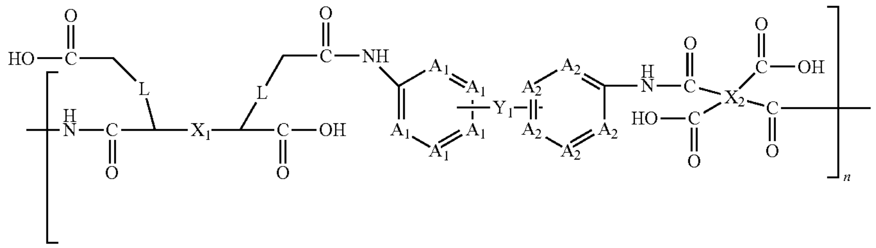

(4)

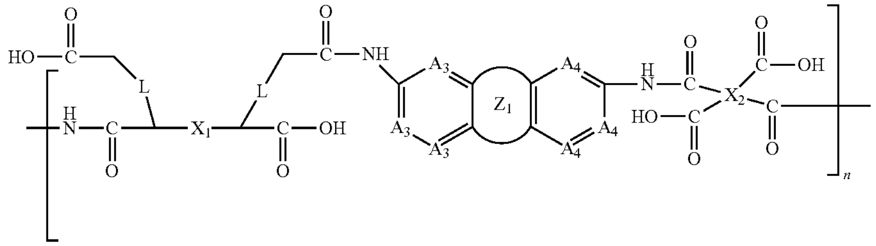

It can be seen from the above structures that, the polyamic acid is still formed by alternately arranging the amorphous soft segments and the amorphous hard segments, and by adjusting the ratio of the first dianhydride to the second dianhydride, lengths of the soft segment and the hard segment in the polyamic acid may be adjusted, and in turn, the hardness, the toughness and brittleness of the polyamic acid may be adjusted, so that the polyamic acid may have good toughness while having certain hardness. Consequently, it may also be possible to solve the problem in the related art that although the polyimide has good hardness (which may be up to 3 H to 4 H), it is easy to generate debris and damage the rubbing cloth due to the excessively high hardness during the rubbing alignment, causing the falling off of the components of the rubbing cloth, and the defect of debris.

Moreover, in a case where the hydrophilicity or hydrophobicity of the polyamic acid is adjusted by introducing the hydrophilic group and the hydrophobic group into the first dianhydride and the first diamine, respectively, or by setting the first soft segment as the hydrophilic segment or the hydrophobic segment, by adjusting the ratio of the first dianhydride to the second dianhydride, the technical effect that the polyamic acid may have an appropriate hydrophilicity or hydrophobicity may also be achieved, cleanness of the polyamic acid may be improved before the cell is formed, the debris generated during the rubbing alignment may be effectively removed, and the defect of debris may also be avoided.

In some embodiments, a molar ratio of the first dianhydride to the second dianhydride may be in a range from 10:90 to 90:10, inclusive.

Based on the above structures, in some other embodiments, $X_2$ in the second dianhydride may be any one selected from the following structures:

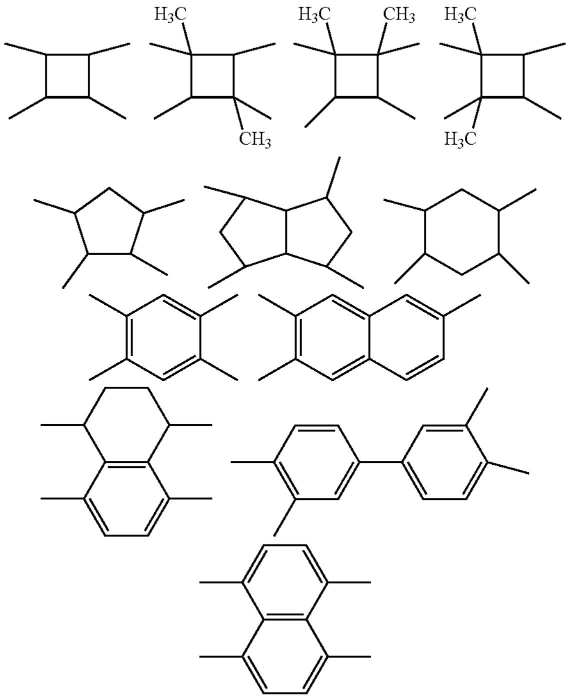

In yet some other embodiments, the following structural formula is selected as $X_2$ in the second dianhydride, in which $R_3$ and $R_4$ are each any one independently selected from hydrogen and an aliphatic hydrocarbon group.

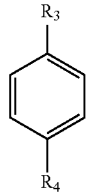

In these embodiments, a structural formula of the second dianhydride is shown as the following formula:

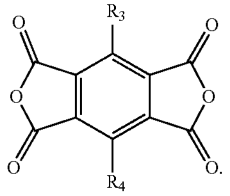

Embodiment 3 of the present disclosure provides a liquid crystal aligning agent including at least one polymer selected from at least one of a polyamic acid and a group of polyimides obtained by ring closure of the polyamic acid. In addition to the first segment structure formed by reacting the first dianhydride represented by the above formula (I) with the first diamine represented by the above formula (II) or formula (III), the polyamic acid further includes a third segment structure formed by reacting a second diamine represented by the following formula with the first dianhydride.

(V)

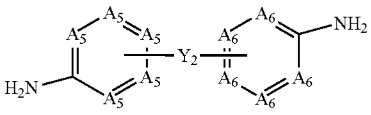

Where $Y_2$ in the second diamine is a second soft segment; C is selected as each of a single $A_5$ and a single $A_6$, and the single $A_5$ and the single $A_6$ are both combined with $Y_2$; the remaining $A_5$s and the remaining $A_6$s are each any one independently selected from CH, CR and N, and neither of the number of Ns in the remaining $A_5$s and the number of Ns in the remaining $A_6$s is more than two; R is any one selected from hydrogen and an aliphatic hydrocarbon group.

In this embodiment, by introducing the second diamine in the presence of the first dianhydride and the first diamine, since $Y_2$ in the second diamine is the second soft segment, the second diamine is used as a soft segment in the third segment structure formed by reacting the second diamine with the first dianhydride. In addition, by controlling crystallinity of the second soft segment, and by adjusting a ratio of the first diamine to the second diamine on the basis that the dianhydride and the diamine are polymerized in the molar ratio of 1:1, a ratio of the first segment structure formed by the first dianhydride and the first diamine to the third segment structure formed by the first dianhydride and the second diamine (i.e., a ratio between segment structures (which may be represented by the following formula (5) or formula (6) depending on different structures of the first diamine) in the polyamic acid, which are obtained by polymerizing the first dianhydride and the second dianhydride with the same first diamine) may be adjusted.

hydrophobic segment and the segment including the at least one hydrophobic group, or then one or two of the at least one substituent group in $Y_1$, the first soft segment and the second soft segment are each any one selected from the hydrophilic (5)

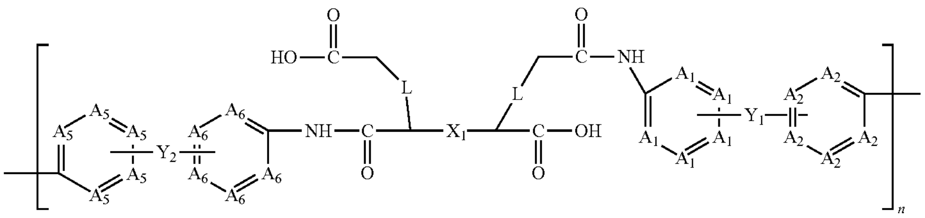

(6)

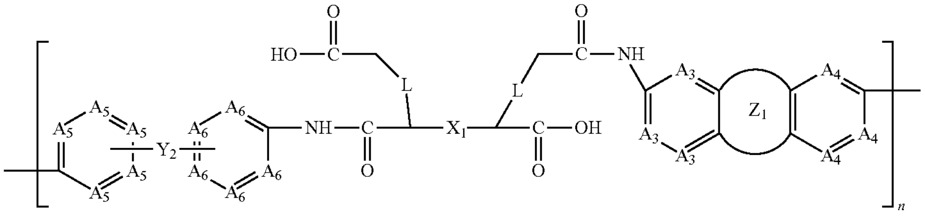

It can be seen from the above structures that, the polyamic acid is still formed by alternately arranging the amorphous soft segments and the amorphous hard segments, and by adjusting the ratio of the first diamine to the second diamine, crystallinity of the polyamic acid may be adjusted, so that the polyamic acid may have good toughness while having certain hardness. Consequently, it may also be possible to solve the problem in the related art that although the polyimide has good hardness (which may be up to 3 H to 4 H), it is easy to generate debris and damage the rubbing cloth due to the excessively high hardness during the rubbing alignment, causing the falling off of the components of the rubbing cloth, and the defect of debris.

Based on the above structures, in some embodiments, if the structure represented by formula (II) is selected as the first diamine, and $Y_1$ is any one selected from a single bond, O, NH, S, one or more unsaturated double bonds, an unsubstituted aliphatic ring, an unsubstituted aromatic ring, an unsubstituted heterocyclic ring and an unsubstituted fused ring, or if the structure represented by formula (III) is selected as the first diamine, and $Z_1$ is any one selected from an unsubstituted aliphatic ring, aromatic ring, heterocyclic ring and fused ring, then at least one of the first soft segment and the second soft segment is any one selected from a hydrophilic segment and a segment including at least one hydrophilic group.

If the structure represented by formula (II) is selected as the first diamine, and $Y_1$ is any one selected from the substituted aliphatic ring, the substituted aromatic ring, the substituted heterocyclic ring and the substituted fused ring, then a hydrophilic group is selected as at least one substituent group in $Y_1$, and the first soft segment and the second soft segment are each any one independently selected from a hydrophobic segment, a segment including at least one hydrophobic group, a hydrophilic segment and a segment including at least one hydrophilic group, or then a hydrophobic group is selected as the at least one substituent group in $Y_1$, and at least one of the first soft segment and the second soft segment is any one selected from the hydrophilic segment and the segment including the at least one hydrophilic group, and the other is any one selected from the segment and the segment including the at least one hydrophilic group, and the remaining two are each or the remaining one is any one selected from the hydrophobic segment and the segment including the at least one hydrophobic group.

In a case where the structure represented by formula (III) is selected as the first diamine, and $Z_1$ is any one selected from the substituted aliphatic ring, the substituted aromatic ring, the substituted heterocyclic ring and the substituted fused ring, then the hydrophilic group is selected as at least one substituent group in $Z_1$, and the first soft segment and the second soft segment are each any one independently selected from the hydrophobic segment, the segment including the at least one hydrophobic group, the hydrophilic segment and the segment including the at least one hydrophilic group, or then the hydrophobic group is selected as the at least one substituent group in $Z_1$, and at least one of the first soft segment and the second soft segment is any one selected from the hydrophilic segment and the segment including the at least one hydrophilic group, and the other is any one selected from the hydrophobic segment and the segment including the at least one hydrophobic group, or then one or two of the at least one substituent group in $Z_1$, the first soft segment and the second soft segment are each any one selected from the hydrophilic segment and the segment including the at least one hydrophilic group, and the remaining two are each or the remaining one is any one selected from the hydrophobic segment and the segment including at least one hydrophobic group.

In these embodiments, on the basis that a hydrophilic group and a hydrophobic group are introduced into the first dianhydride and the first diamine, respectively, or the first soft segment is set to be the hydrophilic segment or the hydrophobic segment, a hydrophilic group or a hydrophobic group is introduced into the second diamine, or the second soft segment is set to be a hydrophilic segment or a hydrophobic segment. By adjusting the ratio of the first diamine to the second diamine, the technical effect that the polyamic acid may have an appropriate hydrophilicity or hydrophobicity may also be achieved, the cleanness of the polyamic acid may be improved before the cell is formed, the debris generated during the rubbing alignment may be effectively removed, and the defect of debris may also be avoided.

Based on the above structures, in some other embodiments, the second soft segment is a substituted or unsubstituted alkylene segment having 5 to 12 carbon atoms. That is, in a case where the second soft segment is an unsubstituted alkylene segment having 5 to 12 carbon atoms, the second soft segment is a hydrophobic segment. In this case, if the structure represented by formula (II) is selected as the first diamine, and $Y_1$ is any one selected from an unsubstituted aliphatic ring, an unsubstituted aromatic ring, an unsubstituted heterocyclic ring and an unsubstituted fused ring, then the first soft segment may be any one selected from a hydrophilic segment and a segment including at least one hydrophilic group; if the structure represented by formula (II) is selected as the first diamine, and $Y_1$ is any one selected from a substituted aliphatic ring, an substituted aromatic ring, an substituted heterocyclic ring and an substituted fused ring, then if a hydrophilic group is selected as the at least one substituent group in $Y_1$, then the first soft segment is any one selected from a hydrophobic segment, a segment including at least one hydrophobic group, the hydrophilic segment and the segment including the at least one hydrophilic group; and if a hydrophobic group is selected as the at least one substituent group in $Y_1$, then the first soft segment is any one selected from the hydrophilic segment and the segment including the at least one hydrophilic group, or at least one of the at least one substituent group in $Y_1$ and the first soft segment is any one selected from the hydrophilic segment and the segment including the at least one hydrophilic group, and the other is any one selected from the hydrophobic segment and the segment including the at least one hydrophobic group.

In yet some other embodiments, the second soft segment is an unsubstituted alkylene segment having 7 carbon atoms. That is, the second soft segment is a hydrophobic segment.

Based on the above structures, in yet some other embodiments, a molar ratio of the first diamine to the second diamine may be in a range from 10:90 to 90:10, inclusive.

Embodiment 4 of the present disclosure provides a liquid crystal aligning agent including at least one polymer selected from at least one of a polyamic acid and a group of polyimides obtained by ring closure of the polyamic acid. The polyamic acid includes at least two segment structures of the third segment structure formed by the first dianhydride represented by the following formula (I) and the second diamine represented by the following formula (V), a fourth segment structure formed by reacting the second diamine represented by the following formula (V) with the second dianhydride represented by the following formula (IV), and the second segment structure formed by the first diamine represented by the following formula (II) or formula (III) and the second dianhydride represented by the following formula (IV).

(I)

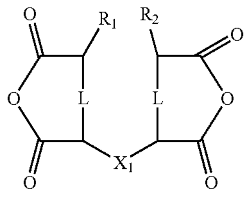

-continued (II)

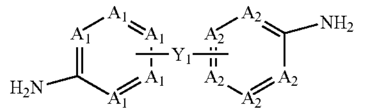

(III)

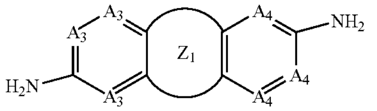

(IV)

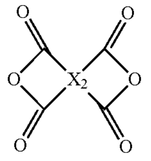

(V)

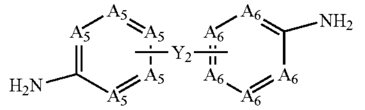

Where $X_1$ in the first dianhydride is a first soft segment, $Y_2$ in the second diamine is a second soft segment, and at least one of the first soft segment and the second soft segment is an amorphous segment; L in the first dianhydride is any one selected from a single bond, a double bond and a divalent or trivalent hydrocarbon group having 1 to 3 carbon atoms;

$X_2$ in the second dianhydride is any one selected from a substituted or unsubstituted aliphatic ring, a substituted or unsubstituted aromatic ring, a substituted or unsubstituted heterocyclic ring and a substituted or unsubstituted fused ring.

In the first diamine represented by formula (II), $Y_1$ is any one selected from a single bond, O, NH, S, one or more unsaturated double bonds, a substituted or unsubstituted aliphatic ring, a substituted or unsubstituted aromatic ring, a substituted or unsubstituted heterocyclic ring and a substituted or unsubstituted fused ring; C is selected as each of a single $A_1$ and a single $A_2$, and the single $A_1$ and the single $A_2$ are both combined with $Y_1$; the remaining $A_1$s and the remaining $A_2$s are each any one independently selected from CH, CR and N, and neither of the number of Ns in the remaining $A_1$s and the number of Ns in the remaining $A_2$s is more than two.

In the first diamine represented by formula (III), $Z_1$ is any one selected from a substituted or unsubstituted aliphatic ring, a substituted or unsubstituted aromatic ring, a substituted or unsubstituted heterocyclic ring and a substituted or unsubstituted fused ring; $A_3$s and $A_4$s are each any one independently selected from CH, CR and N, and neither of the number of Ns in the $A_3$s and the number of Ns in the $A_4$s is more than two.

In the second diamine, C is selected as each of a single $A_5$ and a single $A_6$, and the single $A_5$ and the single Ae are both combined with X2; the remaining $A_5$s and the remaining $A_6$s are each any one independently selected from CH, CR and N, and neither of the number of Ns in the remaining $A_5$s and the number of Ns in the remaining $A_6$s is more than two.

$R_1$, $R_2$ and R are each any one independently selected from hydrogen and the aliphatic hydrocarbon group.

It will be noted that, as for description of the above molecular structure in Embodiment 4 and Embodiment 5 to be described below, reference may be made to the description of Embodiments 1, 2 and 3, and details will not be repeated herein. In the following description, only differences between Embodiments 4 and 5 and Embodiments 1, 2 and 3 will be described.

third segment structure and the fourth segment structure (which may be represented by the following formula (10) or formula (11) depending on different structures of the first diamine).

(7)

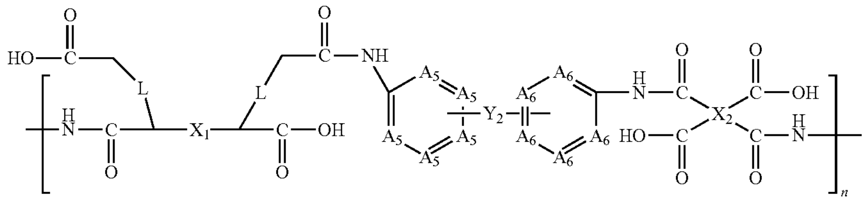

(8)

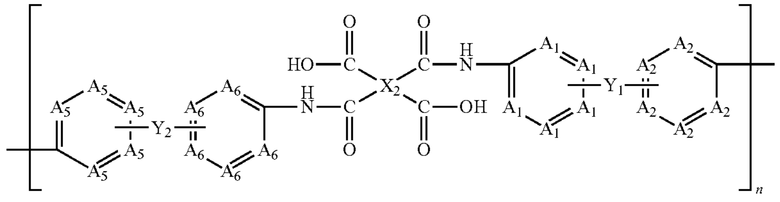

(9)

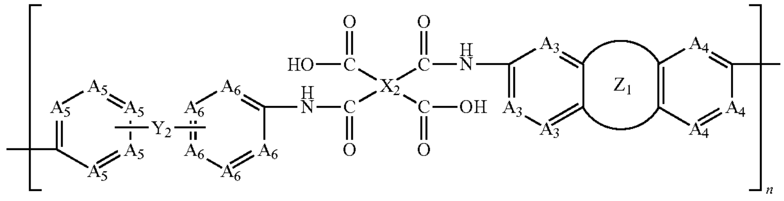

(10)

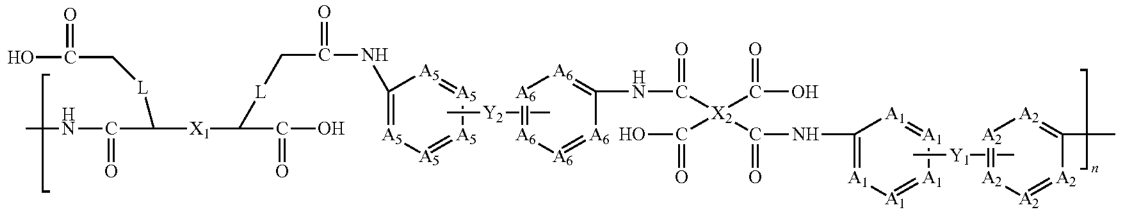

(11)

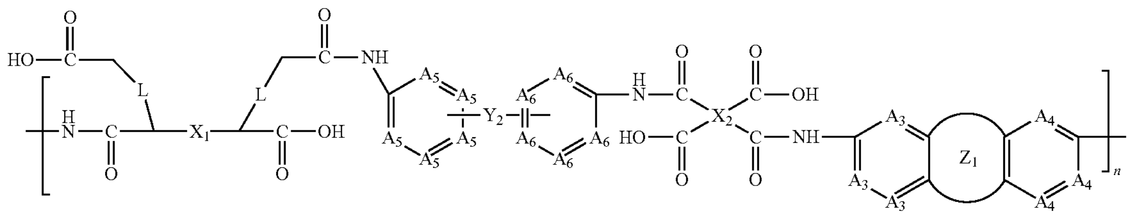

In this embodiment, the polyamic acid may include a segment structure constituted by the third segment structure and the fourth segment structure (i.e., a segment structure (which may be represented by the following formula (7)) in the polyamic acid, which is obtained by polymerizing the first dianhydride and the second dianhydride with a same second diamine); or the polyamic acid may include a segment structure constituted by the second segment structure and the fourth structure (i.e., a segment structure (which may be represented by the following formula (8) or formula (9) depending on different structures of the first diamine) in the polyamic acid, which is obtained by polymerizing the first diamine and the second diamine with a same second dianhydride); or the polyamic acid may include a segment structure constituted by the second segment structure, the It can be seen from the above structures that, the polyamic acid is still formed by alternately arranging the soft segments and the hard segments, and at least one of the first soft segment and the second soft segment is the amorphous segment. Therefore, by reasonably proportioning the soft segments and the hard segments in the molecular structure, the polyamic acid may be endowed with special properties. For example, the toughness of the polyamic acid may be improved while the polyamic acid has good rigidity. For the polyimide in the related art, although it has good hardness (which may be up to 3 H to 4 H), it is easy to generate debris and damage the rubbing cloth due to the excessively high hardness during the rubbing alignment, causing the falling off of the components of the rubbing cloth. Compared with the polyimide in the related art, the polyamic acid has good toughness, and thus when the rubbing cloth is used for rubbing during the rubbing alignment, the product (polyimide) obtained after baking the polyamic acid has good ductility, and may well buffer the external force generated by the rubbing cloth. Consequently, the polyimide itself is not easy to generate debris, and the polyimide is not easy to damage the rubbing cloth, and in turn, the defect of debris may be effectively avoided.

Based on the above structures, in some embodiments, there is a case where the polyamic acid includes the third segment structure formed by the first dianhydride represented by formula (I) and the second diamine represented by formula (V), and the fourth segment structure formed by reacting the second dianhydride represented by formula (IV) with the second diamine represented by formula (V).

In this case, if $X_2$ in the second dianhydride is any one selected from an unsubstituted aliphatic ring, an unsubstituted aromatic ring, an unsubstituted heterocyclic ring and an unsubstituted fused ring, then the first soft segment and the second soft segment are each any one independently selected from a hydrophilic segment, a hydrophobic segment, a segment including at least one hydrophilic group and a segment including at least one hydrophobic group.

In this case, if $X_2$ in the second dianhydride is any one selected from a substituted aliphatic ring, aromatic ring, heterocyclic ring and fused ring, then at least one substituent group in $X_2$ is any one selected from a hydrophobic group and a hydrophilic group, and the first soft segment and the second soft segment are each any one independently selected from a hydrophilic segment and a segment including at least one hydrophilic group, or then a hydrophobic group is selected as the at least one substituent group in $X_2$, and one of the first soft segment and the second soft segment is any one selected from the hydrophilic segment and the segment including the at least one hydrophilic group, and the other is any one selected from the hydrophobic segment and the segment including the at least one hydrophobic group, or then one or two of the at least one substituent group in $X_2$, the first soft segment and the second soft segment are each any one selected from the hydrophilic segment and the segment including the at least one hydrophilic group, and the remaining two are each or the remaining one is any one selected from the hydrophobic segment and the segment including the least one hydrophobic group.

There is a case where the polyamic acid includes the fourth segment structure formed by reacting the second dianhydride represented by formula (IV) with the second diamine represented by formula (V), and the second segment structure formed by the second dianhydride represented by formula (IV) and the first diamine represented by formula (II) or formula (III).

In this case, if the structure represented by formula (II) is selected as the first diamine, and $Y_1$ is any one selected from a single bond, O, NH, S, one or more unsaturated double bonds, an unsubstituted aliphatic ring, an unsubstituted aromatic ring, an unsubstituted heterocyclic ring and an unsubstituted fused ring, or if the structure represented by formula (III) is selected as the first diamine, and $Z_1$ is any one selected from an unsubstituted aliphatic ring, an unsubstituted aromatic ring, an unsubstituted heterocyclic ring and an unsubstituted fused ring, and $X_2$ is any one selected from an unsubstituted aliphatic ring, an unsubstituted aromatic ring, an unsubstituted heterocyclic ring and an unsubstituted fused ring, then the second soft segment is any one selected from a hydrophilic segment and a segment including at least one hydrophilic group.

In this case, if the structure represented by formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then a hydrophilic group is selected as the at least one substituent group in $X_2$, and the second soft segment is any one selected from the hydrophobic segment, the segment including the at least one hydrophobic group, the hydrophilic segment and the segment including the at least one hydrophilic group, or then the hydrophobic group is selected as the at least one substituent group in $X_2$, and the second soft segment is any one selected from the hydrophilic segment and the segment including the at least one hydrophilic group, or then at least one of the at least one substituent group in $X_2$ and the second soft segment is any one selected from the hydrophilic segment and the segment including the at least one hydrophilic group, and the other is any one selected from the hydrophobic segment and the segment including the at least one hydrophobic group.

In this case, if the structure represented by formula (II) is selected as the first diamine, and $Y_1$ is any one selected from the substituted aliphatic ring, the substituted aromatic ring, the substituted heterocyclic ring and the substituted fused ring, or if the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the unsubstituted aliphatic ring, the unsubstituted aromatic ring, the unsubstituted heterocyclic ring and the unsubstituted fused ring, then the at least one substituent group in $Y_1$ or $Z_1$ is the hydrophilic group, and the second soft segment is any one selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the second soft segment is any one selected from the hydrophilic segment and the segment including the at least one hydrophilic group, or then at least one of the at least one substituent group in $Y_1$ or $Z_1$ and the second soft segment is any one selected from the hydrophilic segment and the segment including the at least one hydrophilic group, and the other is any one selected from the hydrophobic segment and the segment including the at least one hydrophobic group.

In this case, if the structure represented by formula (II) is selected as the first diamine, and $Y_1$ is any one selected from the substituted aliphatic ring, the substituted aromatic ring, the substituted heterocyclic ring and the substituted fused ring, or if the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then the at least one substituent group in $Y_1$ or $Z_1$ is the hydrophilic group, and the at least one substituent group in $X_2$ is any one selected from the hydrophilic group and the hydrophobic group, and the second soft segment is any one selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the hydrophilic group is selected as the at least one substituent group in $X_2$, and the second soft segment is any one selected from the hydrophobic segment, the segment including the at least one hydrophobic group, the hydrophilic segment and the segment including the at least one hydrophilic group, or then the hydrophobic group is selected as each of the at least one substituent group in $Y_1$ or $Z_1$ and the at least one substituent group in $X_2$, and the second soft segment is any one selected from the hydrophilic segment and the segment including the at least one hydrophilic group, or then at least one of the at least one substituent group in $Y_1$ or $Z_1$, the at least one substituent group in $X_2$ and the second soft segment is any one selected from the hydrophilic segment and the segment including the at least one hydrophilic group, and the remaining two are each or the remaining one is any one selected from the hydrophobic segment and the segment including the at least one hydrophobic group.

There is a case where the polyamic acid includes the third segment structure formed by the first dianhydride represented by formula (I) and the second diamine represented by formula (V), and the second segment structure formed by the second dianhydride represented by formula (IV) and the first diamine represented by formula (II) or formula (III).

In this case, if the structure represented by formula (II) is selected as the first diamine, and $Y_1$ is any one selected from a single bond, O, NH, S, one or more unsaturated double bonds, and an unsubstituted aliphatic ring, an unsubstituted aromatic ring, an unsubstituted heterocyclic ring and an unsubstituted fused ring, or if the structure represented by formula (III) is selected as the first diamine, and $Z_1$ is any one selected from an unsubstituted aliphatic ring, an unsubstituted aromatic ring, an unsubstituted heterocyclic ring and an unsubstituted fused ring, and $X_2$ is any one selected from an unsubstituted aliphatic ring, an unsubstituted aromatic ring, an unsubstituted heterocyclic ring and an unsubstituted fused ring, then at least one of the first soft segment and the second soft segment is any one selected from a hydrophilic segment and a segment including at least one hydrophilic group, and the other is any one selected from a hydrophobic segment and a segment including at least one hydrophobic group.

In this case, if the structure represented by formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the substituted aliphatic ring, the substituted aromatic ring, the substituted heterocyclic ring and the substituted fused ring, then the at least one substituent group in $X_2$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $X_2$ is the hydrophobic group, and at least one of the first soft segment and second soft segment is any one selected from the hydrophilic segment and the segment including the at least one hydrophilic group, and the other is any one selected from the hydrophobic segment and the segment including the at least one hydrophobic group, or then at least one of the at least one substituent group in $X_2$, the first soft segment and the second soft segment is any one selected from the hydrophilic segment and the segment including the at least one hydrophilic group, and the remaining two are each or the remaining one is any one selected from the hydrophobic segment and the segment including the at least one hydrophobic group.

In this case, if the structure represented by formula (II) is selected as the first diamine, and $Y_1$ is any one selected from the substituted aliphatic ring, the substituted aromatic ring, the substituted heterocyclic ring and the substituted fused ring, or if the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the unsubstituted aliphatic ring, the unsubstituted aromatic ring, the unsubstituted heterocyclic ring and the unsubstituted fused ring, then the at least one substituent group in $Y_1$ or $Z_1$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and at least one of the first soft segment and the second soft segment is any one selected from the hydrophilic segment and the segment including the at least one hydrophilic group, and the other is any one selected from the hydrophobic segment and the segment including the at least one hydrophobic group, or then at least one of the at least one substituent group in $Y_1$ or $Z_1$, the first soft segment and the second soft segment is any one selected from the hydrophilic segment and the segment including the at least one hydrophilic group, and the remaining two are each or the remaining one is any one selected from the hydrophobic segment and the segment including the at least one hydrophobic group.

In this case, if the structure represented by formula (II) is selected as the first diamine, and $Y_1$ is any one selected from the substituted aliphatic ring, the substituted aromatic ring, the substituted heterocyclic ring and the substituted fused ring, or if the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then the at least one substituent group in $Y_1$ or $Z_1$ is the hydrophilic group, and the at least one substituent group in $X_2$ is any one selected from the hydrophilic group and the hydrophobic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the hydrophilic group is selected as the at least one substituent group in $X_2$, and the first soft segment and the second soft segment are each any one independently selected from the hydrophobic segment, the segment including the at least one hydrophobic group, the hydrophilic segment and the segment including the at least one hydrophilic group, or then the hydrophobic group is selected as each of the at least one substituent group in $Y_1$ or $Z_1$ and the at least one substituent group in $X_2$, and at least one of the first soft segment and the second soft segment is any one selected from the hydrophilic segment and the segment including the at least one hydrophilic group, and the other is any one selected from the hydrophobic segment and the segment including the at least one hydrophobic group, or then one, two or three of the at least one substituent group in $Y_1$ or $Z_1$, the at least one substituent group in $X_2$, the first soft segment and the second soft segment are each any one selected from the hydrophilic segment and the segment including the at least one hydrophilic group, and the remaining three or the remaining two are each or the remaining one is any one selected from the hydrophobic segment and the segment including the at least one hydrophobic group.

In these embodiments, by introducing the hydrophilic group and the hydrophobic group into the first dianhydride, the second dianhydride and the second diamine, or by introducing the hydrophilic group and the hydrophobic group into the second dianhydride, the first diamine and the second diamine, or by introducing the hydrophilic group and the hydrophobic group into the first dianhydride, the second dianhydride, the first diamine and the second diamine, the hydrophilicity or hydrophobicity of the polyamic acid finally formed may be adjusted, and it may also be possible to achieve the technical effects that the polyamic acid may have an appropriate hydrophilicity or hydrophobicity, the cleanness of the polyamic acid may be improved before the cell is formed, the debris generated during the rubbing alignment may be effectively removed, and the defect of debris may be avoided.

In some other embodiments, the first soft segment is a substituted or unsubstituted alkylene segment having 10 to 20 carbon atoms; the structure represented by formula (II) is selected as the first diamine, and $Y_1$ is any one selected from an aromatic ring, a heterocyclic ring and a fused ring, in each of which at least one carbon atom is substituted, and at least one substituent group is any one selected from a hydrophilic group and a hydrocarbon group having 1 to 3 carbon atoms and having at least one hydrophilic group; the second soft segment is any one of a hydrophobic segment and a segment including at least one hydrophobic group.

In these embodiments, in a case where the first soft segment is the unsubstituted alkylene segment having 10 to 20 carbon atoms, the first soft segment is a hydrophobic segment. In this case, a ratio among the first dianhydride, the second dianhydride, the first diamine and the second diamine may be controlled, so as to adjust the hydrophilicity or hydrophobicity of the polyamic acid finally formed.

There are two possible cases: in a first case, the first dianhydride has an asymmetrical structure; and in a second case, the first soft segment includes asymmetrical branches.

In the first case where the first dianhydride has the asymmetrical structure, as for description of the asymmetrical structure, reference may be made to the above description that the first dianhydride has an asymmetrical structure, and details will not be repeated here. In this case, the first soft segment may be the unsubstituted alkylene segment having 10 to 20 carbon atoms. In this case, the first soft segment is an amorphous segment.

In the second case, the first soft segment includes asymmetrical branches. In this case, the first soft segment may be the substituted alkylene segment having 10 to 20 carbon atoms. As for specific description of the asymmetrical branches, reference may be made to the above description of the asymmetrical branches, and details will not be repeated here. In this case, the first soft segment is also the amorphous segment.

In yet some other embodiments, the second soft segment is a substituted or unsubstituted alkylene segment having 5 to 12 carbon atoms.

In these embodiments, there are two possible cases: in a first case, the first diamine has an asymmetrical structure; and in a second case, the second soft segment includes asymmetrical branches.

In the first case, the first diamine has the asymmetrical structure. That is, $Y_1$ may be bonded to different positions (which, e.g., are not both ortho-positions, meta-positions or para-positions) of amino groups in two benzene rings, or the numbers and positions of CRs, or structures of Rs in the two benzene rings are different. In this case, the second soft segment may be the unsubstituted alkylene segment having 5 to 12 carbon atoms. In this case, the second soft segment is an amorphous segment.

In the second case, the second soft segment includes asymmetrical branches. That is, the second soft segment is the substituted alkylene segment having 5 to 12 carbon atoms, and substituent groups form asymmetrical branches. In this case, the second soft segment is also the amorphous segment. A position of $Y_1$, and the numbers and positions of CRs and structures of Rs in the two benzene rings are not specifically limited.

In yet some other embodiments, in the first diamine, $Y_1$ is bonded to a para-position of an amino group, and a benzene ring in which a carbon atom is substituted is selected as $Y_1$, and an alcoholic hydroxyl group having 1 to 3 carbon atoms is selected as a substituent group.

That is, in these embodiments, since $Y_1$ is bonded to the para-position of the amino group, in a case where the $A_1$s and the $A_2$s are each any one independently selected from CH and CR, the first diamine is terphenyl, and the hydrophilic group is an alcoholic hydroxyl group.

Embodiment 5 of the present disclosure provides a liquid crystal aligning agent including at least one polymer selected from at least one of a polyamic acid and a group of polyimides obtained by ring closure of the polyamic acid. The polyamic acid includes the first segment structure formed by the first dianhydride represented by the following formula (I) and the first diamine represented by the following formula (II) or formula (III), the second segment structure formed by the second dianhydride represented by the following formula (IV) and the first diamine represented by the following formula (II) or formula (III), the third segment structure formed by the first dianhydride represented by the following formula (IV) and the second diamine represented by the following formula (V), and the fourth segment structure formed by the second dianhydride represented by the following formula (IV) and the second diamine represented by the following formula (V).

(I)

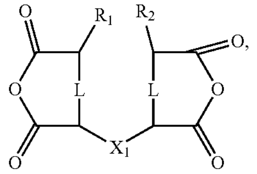

-continued (II)

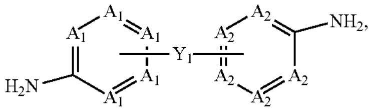

and (III)

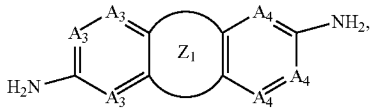

(IV)

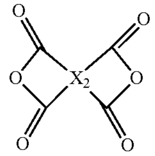

(V)

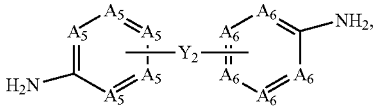

Where $X_1$ in the first dianhydride is a first soft segment, $Y_2$ in the second diamine is a second soft segment, and at least one of the first soft segment and the second soft segment is an amorphous segment; L in the first dianhydride is any one selected from a single bond, a double bond and a divalent or trivalent hydrocarbon group having 1 to 3 carbon atoms;

$X_2$ in the second dianhydride is any one selected from a substituted or unsubstituted aliphatic ring, a substituted or unsubstituted aromatic ring, a substituted or unsubstituted heterocyclic ring and a substituted or unsubstituted fused ring.

In the first diamine represented by formula (II), $Y_1$ is any one selected from a single bond, O, NH, S, one or more unsaturated double bonds, and a substituted or unsubstituted aliphatic ring, a substituted or unsubstituted aromatic ring, a substituted or unsubstituted heterocyclic ring and a substituted or unsubstituted fused ring; C is selected as each of a single $A_1$ and a single $A_2$, and the single $A_1$ and the single $A_2$ are both combined with $Y_1$; the remaining $A_1$s and the remaining $A_2$s are each any one independently selected from CH, CR and N, and neither of the number of Ns in the remaining $A_1$s and the number of Ns in the remaining $A_2$s is more than two.

In the first diamine represented by formula (III), $Z_1$ is any one selected from a substituted or unsubstituted aliphatic ring, a substituted or unsubstituted aromatic ring, a substituted or unsubstituted heterocyclic ring and a substituted or unsubstituted fused ring; $A_3$s and $A_4$s are each any one independently selected from CH, CR and N, and neither of the number of Ns in the $A_3$s and the number of Ns in the $A_4$s is more than two.

In the second diamine, C is selected as each of a single $A_5$ and a single $A_6$, and the single $A_5$ and the single $A_6$ are both combined with $Y_2$; the remaining $A_5$s and the remaining $A_6$s are each any one independently selected from CH, CR and N, and neither of the number of Ns in the remaining $A_5$s and the number of Ns in the remaining $A_6$s is more than two.

$R_1$, $R_2$ and R are each any one independently selected from hydrogen and an aliphatic hydrocarbon group.

In this embodiment, the polyamic acid may include a segment structure (which may be represented by the following formula (12) or formula (13) depending on different structures of the first diamine) formed by the first segment structure, the second structure, the third structure and the fourth structure, or may include a segment structure formed by the first segment structure and the second segment structure, a segment structure formed by the third segment structure and the fourth segment structure, a segment structure formed by the first segment structure and the third segment structure, and a segment structure (which may be represented by the following formula (14) or formula (15) depending on different structures of the first diamine) formed by the second segment structure and the fourth segment structure.

(12)

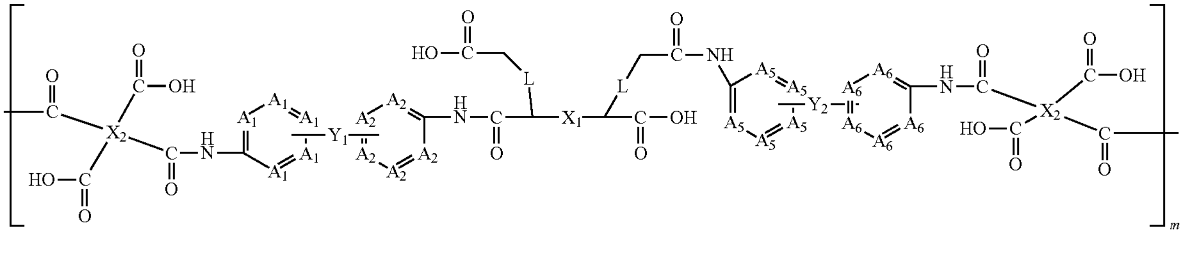

(13)

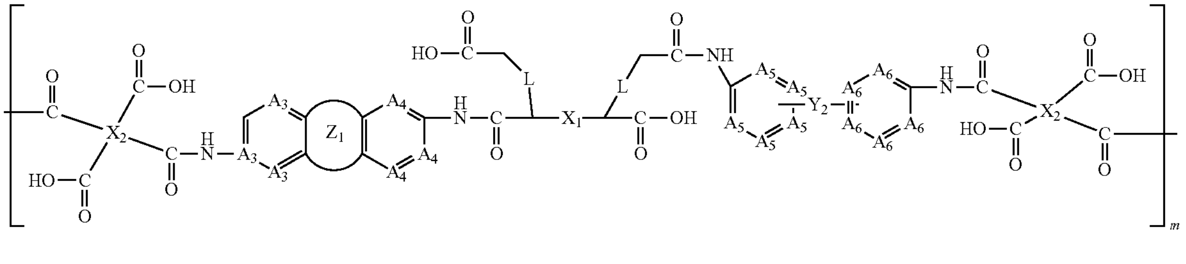

-continued

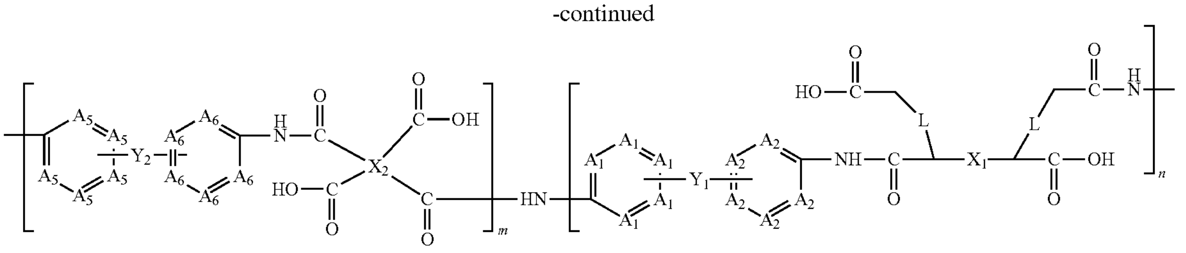

(14)

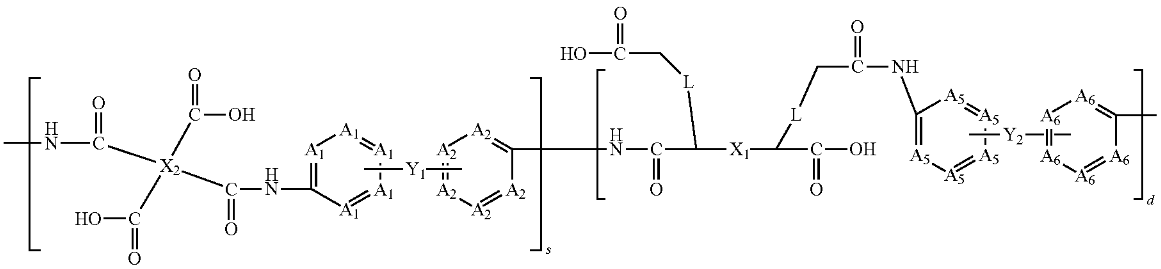

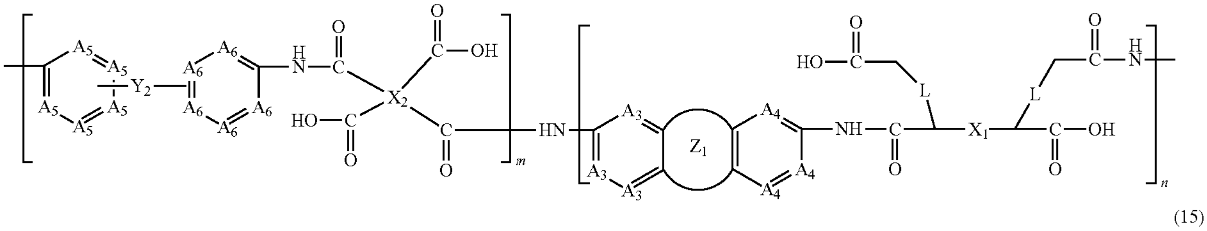

(15)

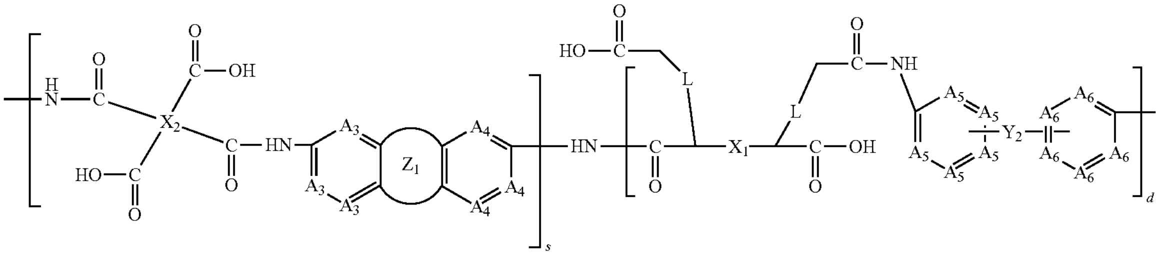

It can be seen from the above structures that, the polyamic acid is formed by alternately arranging the soft segments and the hard segments, and at least one of the first soft segment and the second soft segment is an amorphous segment. Therefore, by reasonably proportioning the soft segments and the hard segments in the molecular structure, the polyamic acid may be endowed with special properties. For example, the toughness of the polyamic acid may be improved while the polyamic acid has good rigidity. For the polyimide in the related art, although it has good hardness (which may be up to 3 H to 4 H), it is easy to generate debris and damage the rubbing cloth due to the excessively high hardness during the rubbing alignment, causing the falling off of the components of the rubbing cloth. Compared with the polyimide in the related art, the polyamic acid has good toughness, and thus when the rubbing cloth is used for rubbing during the rubbing alignment, the product (polyimide) obtained after baking the polyamic acid has good ductility, and may well buffer the external force generated by the rubbing cloth. Consequently, the polyimide itself is not easy to generate debris, and the polyimide is not easy to damage the rubbing cloth, and in turn, the defect of debris may be effectively avoided.

Based on the above structures, in some embodiments, if the structure represented by formula (II) is selected as the first diamine, and $Y_1$ is any one selected from a single bond, O, NH, S, one or more unsaturated double bonds, an unsubstituted aliphatic ring, an unsubstituted aromatic ring, an unsubstituted heterocyclic ring and an unsubstituted fused ring, or if the structure represented by formula (III) is selected as the first diamine, and $Z_1$ is any one selected from an unsubstituted aliphatic ring, an unsubstituted aromatic ring, an unsubstituted heterocyclic ring and an unsubstituted fused ring, and $X_2$ is any one selected from an unsubstituted aliphatic ring, an unsubstituted aromatic ring, an unsubstituted heterocyclic ring and an unsubstituted fused ring, then at least one of the first soft segment and the second soft segment is any one selected from a hydrophilic segment and a segment including at least one hydrophilic group, and the other is any one selected from a hydrophobic segment and a segment including at least one hydrophobic group.

If the structure represented by formula (II) is selected as the first diamine, and $Y_1$ is any one selected from the single bond, O, NH, S, the one or more unsaturated double bonds, the unsubstituted aliphatic ring, the unsubstituted aromatic ring, the unsubstituted heterocyclic ring and the unsubstituted fused ring, or if the structure represented by formula (III) is selected as the first diamine, and $Z_1$ is any one selected from the unsubstituted aliphatic ring, the unsubstituted aromatic ring, the unsubstituted heterocyclic ring and the unsubstituted fused ring, and $X_2$ is any one selected from the substituted aliphatic ring, the substituted aromatic ring, the substituted heterocyclic ring and the substituted fused ring, then the at least one substituent group in $X_2$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $X_2$ is the hydrophobic group, and at least one of the first soft segment and second soft segment is any one selected from the hydrophilic segment and the segment including the at least one hydrophilic group, and the other is any one selected from the hydrophobic segment and the segment including the at least one hydrophobic group, or then at least one of the at least one substituent group in $X_2$, the first soft segment and the second soft segment is any one selected from the hydrophilic segment and the segment including the at least one hydrophilic group, and the remaining two are each or the remaining one is any one selected from the hydrophobic segment and the segment including the at least one hydrophobic group.

If the first diamine is selected as the structure represented by formula (II) is selected as the first diamine, and $Y_1$ is any one selected from the substituted aliphatic ring, the substituted aromatic ring, the substituted heterocyclic ring and the substituted fused ring, or if the first diamine is selected as the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the unsubstituted aliphatic ring, the unsubstituted aromatic ring, the unsubstituted heterocyclic ring and the unsubstituted fused ring, then the at least one substituent group in $Y_1$ or $Z_1$ is the hydrophilic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and at least one of the first soft segment and the second soft segment is any one selected from the hydrophilic segment and the segment including the at least one hydrophilic group, and the other is any one selected from the hydrophobic segment and the segment including the at least one hydrophobic group, or then at least one of the at least one substituent group in $Y_1$ or $Z_1$, the first soft segment and the second soft segment is any one selected from the hydrophilic segment and the segment including the at least one hydrophilic group, and the remaining two are each or the remaining one is any one selected from the hydrophobic segment and the segment including the at least one hydrophobic group.

If the structure represented by formula (II) is selected as the first diamine, and $Y_1$ is any one selected from the substituted aliphatic ring, the substituted aromatic ring, the substituted heterocyclic ring and the substituted fused ring, or if the structure represented by formula (III) is selected as the first diamine, and $Z_1$ is any one selected from the substituted aliphatic ring, the substituted aromatic ring, the substituted heterocyclic ring and the substituted fused ring, and $X_2$ is any one selected from the substituted aliphatic ring, the substituted aromatic ring, the substituted heterocyclic ring and the substituted fused ring, then the at least one substituent group in $Y_1$ or $Z_1$ is the hydrophilic group, and the at least one substituent group in $X_2$ is any one selected from the hydrophilic group and the hydrophobic group, and the first soft segment and the second soft segment are each any one independently selected from the hydrophobic segment, the segment including the at least one hydrophobic group, the hydrophilic segment and the segment including the at least one hydrophilic group, or then the at least one substituent group in $Y_1$ or $Z_1$ is the hydrophobic group, and the hydrophilic group is selected as the at least one substituent group in $X_2$, and the first soft segment and the second soft segment are each any one independently selected from the hydrophobic segment, the segment including the at least one hydrophobic group, the hydrophilic segment and the segment including the at least one hydrophilic group, or then a hydrophobic group is selected as each of the at least one substituent group in $Y_1$ or $Z_1$ and the at least one substituent group in $X_2$, and at least one of the first soft segment and the second soft segment is any one selected from the hydrophilic segment and the segment including the at least one hydrophilic group, and the other is any one selected from the hydrophobic segment and the segment including the at least one hydrophobic group, or then one, two or three of the at least one substituent group in $Y_1$ or $Z_1$, the at least one substituent group in $X_2$, the first soft segment and the second soft segment are each any one selected from the hydrophilic segment and the segment including the at least one hydrophilic group, and the remaining three or the remaining two are each or the remaining one is any one selected from the hydrophobic segment and the segment including the at least one hydrophobic group.

In these embodiments, by introducing the hydrophilic group and the hydrophobic group into the first dianhydride, the second dianhydride, the first diamine and the second diamine, the hydrophilicity or hydrophobicity of the polyamic acid finally formed may be adjusted, and it may also be possible to achieve the technical effects that the polyamic acid may have an appropriate hydrophilicity or hydrophobicity, the cleanness of the polyamic acid may be improved before the cell is formed, the debris generated during the rubbing alignment may be effectively removed, and the defect of debris may be avoided.

In some other embodiments, the first soft segment is a substituted or unsubstituted alkylene segment having 10 to 20 carbon atoms; the structure represented by formula (II) is selected as the first diamine, and $Y_1$ is any one selected from an aromatic ring, a heterocyclic ring and a fused ring, in each of which at least one carbon atom is substituted, and at least one substituent group is any one selected from a hydrophilic group and a hydrocarbon group having 1 to 3 carbon atoms and having at least one hydrophilic group; the second soft segment is any one selected from a hydrophobic segment and a segment including at least one hydrophobic group; the following structural formula is selected as $X_2$ in the second dianhydride, in which $R_3$ and $R_4$ are each any one independently selected from hydrogen and an aliphatic hydrocarbon group.

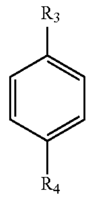

In these embodiments, in a case where the first soft segment is the unsubstituted alkylene segment having 10 to 20 carbon atoms, the first soft segment is a hydrophobic segment. In this case, the ratio among the first dianhydride, the second dianhydride, the first diamine and the second diamine may be controlled, so as to adjust the hydrophilicity or hydrophobicity of the polyamic acid finally formed.

There are two possible cases: in a first case, the first dianhydride has an asymmetrical structure; and in a second case, the first soft segment includes asymmetrical branches.

In the first case where the first dianhydride has the asymmetrical structure, as for description of the asymmetrical structure, reference may be made to the above description that the first dianhydride has an asymmetrical structure, and details will not be repeated here. In this case, the first soft segment may be the unsubstituted alkylene segment having 10 to 20 carbon atoms. In this case, the first soft segment is an amorphous segment.

In the second case, the first soft segment includes asymmetrical branches. In this case, the first soft segment may be a substituted alkylene segment having 10 to 20 carbon atoms. For specific description of the asymmetrical branches, reference may be made to the above description of the asymmetrical branches, and details will not be repeated here. In this case, the first soft segment is also the amorphous segment.

In yet some other embodiments, the second soft segment is a substituted or unsubstituted alkylene segment having 5 to 12 carbon atoms.

In these embodiments, there are two possible cases: in a first case, the first diamine has an asymmetrical structure; and in a second case, the second soft segment includes asymmetrical branches.

In the first case, the first diamine has the asymmetrical structure. That is, $Y_1$ may be bonded to different positions (which, e.g., are not both ortho-positions, meta-positions or para-positions) of amino groups in two benzene rings, or the numbers and positions of CRs, or structures of Rs in the two benzene rings are different. In this case, the second soft segment may be the unsubstituted alkylene segment having 5 to 12 carbon atoms. In this case, the second soft segment is an amorphous segment.

In the second case, the second soft segment includes asymmetrical branches. That is, the second soft segment is the substituted alkylene segment having 5 to 12 carbon atoms, and substituent groups form asymmetrical branches. In this case, the second soft segment is the amorphous segment. A position of $Y_1$, and the numbers and positions of CRs and structures of Rs in the two benzene rings are not specifically limited.

In yet some other embodiments, in the first diamine, $Y_1$ is bonded to a para-position of an amino group, and a benzene ring in which a carbon atom is substituted is selected as $Y_1$, and an alcoholic hydroxyl group having 1 to 3 carbon atoms is selected as the substituent group.

That is, in these embodiments, since $Y_1$ is bonded to the para-position of the amino group, in a case where the $A_1$s and the $A_2$s are each any one independently selected from CH and CR, the first diamine is terphenyl, and the hydrophilic group is an alcoholic hydroxyl group.

Embodiment 6 of the present disclosure provides a liquid crystal aligning agent including at least one polymer selected from at least one of a polyamic acid and a group of polyimides obtained by ring closure of the polyamic acid. The polyamic acid includes a fifth segment structure formed by the second dianhydride represented by the following formula (IV) and the second diamine represented by the following formula (V).

(IV)

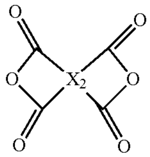

(V)

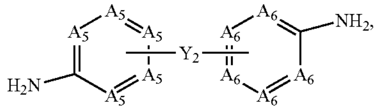

Where $X_2$ in the second dianhydride is any one selected from a substituted or unsubstituted aliphatic ring, a substituted or unsubstituted aromatic ring, a substituted or unsubstituted heterocyclic ring and a substituted or unsubstituted fused ring; $Y_2$ in the second diamine is a second soft segment, and the second soft segment is an amorphous segment; in the second diamine, C is selected as each of a single $A_5$ and a single $A_6$, and the single $A_5$ and the single $A_6$ are both combined with $Y_2$; the remaining $A_5$s and the remaining $A_6$s are each any one independently selected from CH, CR and N, and neither of the number of Ns in the remaining $A_5$s and the number of Ns in the remaining $A_6$s is more than two; R is any one selected from hydrogen and an aliphatic hydrocarbon group.

In a case where $X_2$ in the second dianhydride is any one selected from the unsubstituted aliphatic ring, the unsubstituted aromatic ring, the unsubstituted heterocyclic ring and the unsubstituted fused ring, then the second soft segment is any one selected from a hydrophilic segment and a segment including at least one hydrophilic group.

In a case where $X_2$ in the second dianhydride is any one selected from the substituted aliphatic ring, the substituted aromatic ring, the substituted heterocyclic ring and the substituted fused ring, then the at least one substituent group in $X_2$ is a hydrophilic group, and the second soft segment is any one selected from a hydrophobic segment and a segment including at least one hydrophobic group, or then the at least one substituent group in $X_2$ is a hydrophobic group, and the second soft segment is any one selected from a hydrophilic segment and a segment including at least one hydrophilic group, or then at least one of the at least one substituent group in $X_2$ and the second soft segment is any one selected from the hydrophobic segment and the segment including the at least one hydrophobic group, and the other is any one selected from the hydrophilic segment and the segment including the at least one hydrophilic group.

In this embodiment, by introducing the hydrophilic group and the hydrophobic group into the second dianhydride and the second diamine, the hydrophilicity or hydrophobicity of the polyamic acid may be adjusted, and it may also be possible to achieve the technical effects that the polyamic acid may have an appropriate hydrophilicity or hydrophobicity, the cleanness of the polyamic acid may be improved before the cell is formed, the debris generated during the rubbing alignment may be effectively removed, and the defect of debris may be avoided.

In some embodiments, hardness of the liquid crystal alignment film is characterized by a depth at which a pricking needle pricks into the liquid crystal alignment film under a preset pressure. The hardness of the liquid crystal alignment film satisfies that a value thereof is less than or equal to 45 μm under the preset pressure of 150 ρN.

For example, a Hysitron tribo-indenter (In-situ nano-mechanical test) device may be used, and a probe of the device drives the pricking needle to prick into the liquid crystal alignment film. At the same pressure, the smaller the depth at which the needle is inserted into the alignment film, the greater the hardness of the film is.

In these embodiments, since the value of the hardness of the liquid crystal alignment film is less than or equal to 45 μm, the hardness of the liquid crystal alignment film is improved as compared with the related art in which the value of the hardness of the liquid crystal alignment film is greater than 50 μm under the preset pressure of 150 μN.

In some embodiments, toughness of the liquid crystal alignment film is characterized by a pressure corresponding to an abrupt depth change of the pricking needle in a thickness direction of the liquid crystal alignment film, and a value of the toughness of the liquid crystal alignment film is greater than 390 μN.

Similarly, the Hysitron tribo-indenter device may be used, and the probe of the device drives the pricking needle to prick into the liquid crystal alignment film. When the liquid crystal alignment film is broken and peeled off, the larger the pressure of the probe corresponding to the abrupt depth change of the pricking needle in the thickness direction of the liquid crystal alignment film, the greater the toughness of the film is.

In these embodiments, the toughness of the liquid crystal alignment film is increased as compared with the related art in which the pressure of the probe corresponding to the abrupt depth change of the pricking needle in the thickness direction of the liquid crystal alignment film when the liquid crystal alignment film is broken and peeled off is less than 300 μN.

In some embodiments, in a case where the liquid crystal aligning agent includes a hydrophilic segment and/or a hydrophilic group, a water contact angle of the liquid crystal alignment film is less than or equal to 58 degrees.

By introducing the hydrophilic segment and/or the hydrophilic group, and by adjusting a ratio of the hydrophobic group to the hydrophilic group, the water contact angle of the liquid crystal alignment film may be adjusted, so that an effect of cleaning the debris may be improved.

In some embodiments, in a case where a molar percentage between the first diamine and the second diamine included in the liquid crystal aligning agent is 35%:15%, as the ratio between the first dianhydride and the second dianhydride included in the liquid crystal aligning agent gradually increases, the hardness of the liquid crystal alignment film decreases, and the toughness thereof increases.

By adjusting the ratio of the first dianhydride including a soft segment to the second dianhydride having a rigid structure, the hardness and toughness of the liquid crystal alignment film may be adjusted.

In some embodiments, in a case where the molar percentage between the first dianhydride to the second dianhydride included in the liquid crystal aligning agent is 10%:40%, and $Y_2$ in the second diamine is a hydrophobic segment, as the ratio between the first diamine and the second diamine included in the liquid crystal aligning agent gradually increases, the water contact angle of the liquid crystal alignment film gradually decreases.

By adjusting the ratio between the first diamine and the second diamine, the ratio between the hydrophilic group and the hydrophobic group of the liquid crystal alignment film may be adjusted, so that the water contact angle of the liquid crystal alignment film may be adjusted.

In order to objectively evaluate the beneficial technical effects of the embodiments of the present disclosure, the liquid crystal alignment film provided by the present disclosure will be exemplarily described in detail below through the following experimental examples.

Experimental Example 1

In Experimental Example 1, a dianhydride and a diamine that have been mass-produced at present are used, and structural formulas of the dianhydride and the diamine are shown as the following formula (i) and formula (ii).

(i)

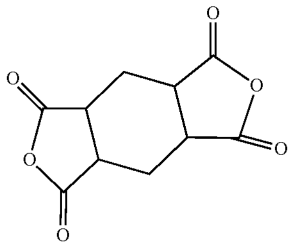

(ii)

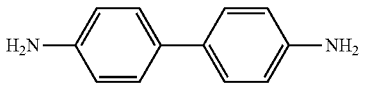

A preparation method is as follows.

In S1, a certain amount of N-methylpyrrolidone or dimethyl formamide (DMF) is added into a reactor, in which nitrogen gas is introduced for protection. The dianhydride represented by formula (i) and the diamine represented by formula (ii) are added and mixed, and are polymerized for 4 h to 6 h while being stirred at a temperature of the reactor controlled in a range from 15° C. to 30° C., inclusive, so as to obtain a polyamic acid A.

In S2, a purified polyamic acid A is diluted with a certain solvent (formed by mixing γ-butyrrolactone (GBL), N-methyl-2-pyrrolidone (NMP), butyl carbitol (BC, also referred to as butyl di-glycol) and diacetone alcohol (DAA) in a ratio of 50:30:10:10), in a mass percentage of the polyamic acid in a range from 3.0% to 4.5%, inclusive, so as to obtain a coating material of the polyamic acid A.

In S3, the polyamic acid A is applied by coating on the base substrate on which the TFT, the pixel electrode and the common electrode have been formed, or on the base substrate on which the color filter layer and the black matrix have been formed, and the polyamic acid A is cured by pre-curing and main curing. Finally, the polyamic acid is dehydrated (amidated) by baking to form a polyimide A.

In S4, a contact-type directional mechanical rubbing is performed on the polyimide A by using a lint roller, and a rotational speed of the roller is controlled in a range from 1000 RPM to 1200 RPM, inclusive, and a moving speed of a base is in a range from 30 mm/s to 40 mm/s, inclusive. The polyimide A is rubbed for alignment to obtain a liquid crystal alignment film after the rubbing alignment, thereby obtaining the array substrate and the opposite substrate. Moreover, the hardness and toughness of the liquid crystal alignment film are measured by using the Hysitron tribo-indenter device, and are marked as a sample a. In addition, an alignment rubbing experiment is performed, and wear resistance of the liquid crystal alignment film is characterized by a number of debris after the rubbing.

A method for measuring the hardness and toughness is as follows: a liquid crystal alignment film with a certain thickness, without the rubbing alignment, is formed on the substrate, the Hysitron tribo-indenter device is used, and the probe of the device drives the pricking needle to prick into the liquid crystal alignment film, and the hardness of the liquid crystal alignment film is characterized by the depth at which the pricking needle pricks into the liquid crystal alignment film under the pressure of the probe of 150 μN; in addition, the Hysitron tribo-indenter device is used, and the probe of the device drives the pricking needle to prick into the liquid crystal alignment film, and drives the pricking needle to move along a horizontal direction, until the toughness of the liquid crystal alignment film is characterized by the pressure of the probe corresponding to the abrupt depth change of the pricking needle in the thickness direction of the liquid crystal alignment film when the liquid crystal alignment film is peeled off and broken.

The number of debris after the rubbing is obtained by randomly selecting a plurality of groups of pixels with a certain number of pixels in each group at different positions of the liquid crystal alignment film under a microscope, and then counting numbers of debris in the groups, and then averaging the numbers of debris by weighting.

In S5, the liquid crystal alignment film after the rubbing alignment is cleaned. In this process, the water contact angle of the liquid crystal alignment film is measured, and a water contact angle measurement sample is marked as the sample a. In addition, cleaning performance of the liquid crystal alignment film is characterized by a removal rate of P/T before and after cleaning, and a cleaning performance characterization sample is marked as the sample a.

Experimental Example 2

In Experimental Example 2, the following various experimental protocols are used. The following experimental protocols are basically same as the preparation process in Experimental Example 1, except that experimental raw materials used in Experimental Example 2 are the dianhydride and the diamine shown below provided by embodiments of the present disclosure.

In a first experimental protocol, experimental raw materials are the first dianhydride represented by the following formula (I) and the first diamine represented by the following formula (II), in which a methyl group is selected as each of $R_1$ and $R_2$.

In a second experimental protocol, experimental raw materials are the first dianhydride represented by the following formula (I) and the first diamine represented by the following formula (III), in which a methyl group is selected as each of $R_1$ and $R_2$.

In a third experimental protocol, experimental raw materials are the first dianhydride represented by the following formula (I), the first diamine represented by the following formula (II) and the second dianhydride represented by the following formula (IV), in which a methyl group is selected as each of $R_1$ and $R_2$, and hydrogen is selected as each of $R_3$ and $R_4$.

In a fourth experimental protocol, experimental raw materials are the first dianhydride represented by the following formula (I), the first diamine represented by the following formula (III) and the second dianhydride represented by the following formula (IV), in which a methyl group is selected as each of $R_1$ and $R_2$, and hydrogen is selected as each of $R_3$ and $R_4$.

In a fifth experimental protocol, experimental raw materials are the first dianhydride represented by the following formula (I), the first diamine represented by the following formula (II) and the second diamine represented by the following formula (V), in which a methyl group is selected as each of $R_1$ and $R_2$. In a sixth experimental protocol, experimental raw materials are the first dianhydride represented by the following formula (I), the first diamine represented by the following formula (III) and the second diamine represented by the following formula (V), in which a methyl group is selected as each of $R_1$ and $R_2$. In a seventh experimental protocol, experimental raw materials are the second dianhydride represented by the following formula (IV), the first diamine represented by the following formula (II) and the second diamine represented by the following formula (V), in which hydrogen is selected as each of $R_3$ and $R_4$.

In an eighth experimental protocol, experimental raw materials are the second dianhydride represented by the following formula (IV), the first diamine represented by the following formula (III) and the second diamine represented by the following formula (V), in which hydrogen is selected as each of $R_3$ and $R_4$.

In a ninth experimental protocol, experimental raw materials are the first dianhydride represented by the following formula (I), the second dianhydride represented by the following formula (IV) and the second diamine represented by the following formula (V), in which a methyl group is selected as each of $R_1$ and $R_2$, and hydrogen is selected as each of $R_3$ and $R_4$.

(I)

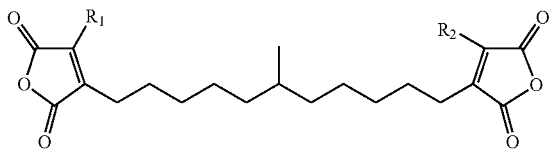

(II)

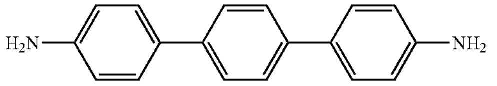

(III)

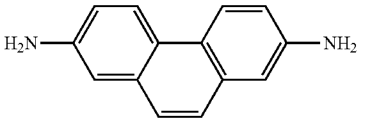

(IV)

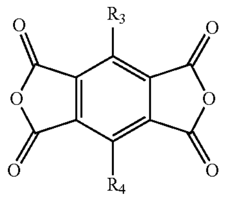

(V)

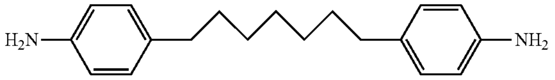

The hardness measured in Experimental Example 1 and the hardness and the toughness measured in the first experimental protocol to the ninth experimental protocol (which are marked as b1 to b9, respectively) are shown in Table 1 below. In addition, comparisons among the Experimental Example 1, and the first experimental protocol to the ninth experimental protocol in the aspects of the measured number of debris after the rubbing, the hardness and the toughness, respectively, are shown in FIG. 5.

TABLE 1

| Experimental | Experimental Example 1 | Experimental Example 2 | | | | | | | | |
|---|---|---|---|---|---|---|---|---|---|---|
| example | a | b1 | b2 | b3 | b4 | b5 | b6 | b7 | b8 | b9 |
| Hardness (μm) | 51 | 39 | 35 | 31 | 29 | 44 | 42 | 28 | 26 | 42 |
| Toughness (μN) | 350 | 420 | 413 | 410 | 405 | 530 | 518 | 393 | 395 | 499 |
| Number of debris (pcs) | 107 | 68 | 72 | 77 | 75 | 60 | 55 | 81 | 79 | 66 |

Figure 5:
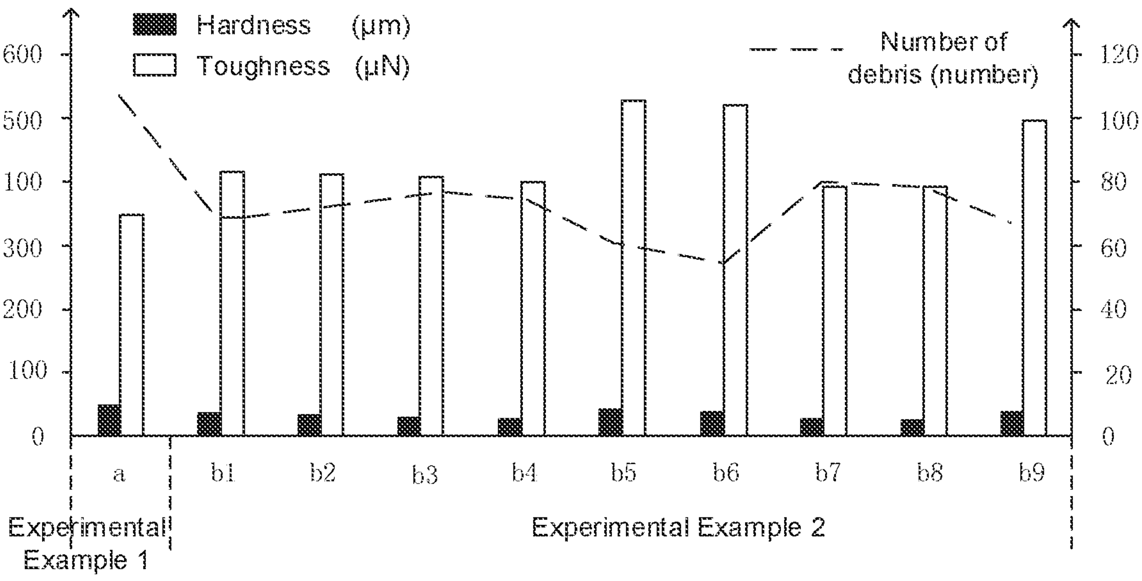
FIG. 5 is a diagram showing comparisons among the sample a, and the samples b1 to b9 in the aspects of the hardness, the toughness and the number of debris, respectively, in accordance with some embodiments.

It can be seen from Table 1 and FIG. 5 that, in the technical solutions of the present disclosure, the polymer is formed by alternately arranging soft segments and hard segments, and the toughness of the liquid crystal alignment film finally obtained may be adjusted by adjusting a ratio of the soft segments to the hard segments, so that the wear resistance of the liquid crystal alignment film may be improved, and the debris may be reduced.

Experimental Example 3

In Experimental Example 3, the following various experimental protocols are used. The following experimental protocols are basically same as Experimental Example 2, except that experimental raw materials used in Experimental Example 3 further include a hydrophobic group and a hydrophilic group.

In a first experimental protocol, experimental raw materials are the first dianhydride represented by the following formula (I) and the first diamine represented by the following formula (II), in which a methyl group is selected as each of $R_1$ and $R_2$.

In a second experimental protocol, experimental raw materials are the first dianhydride represented by the following formula (I) and the first diamine represented by the following formula (III), in which a methyl group is selected as each of $R_1$ and $R_2$.

In a third experimental protocol, experimental raw materials are the first dianhydride represented by the following formula (I), the first diamine represented by the following formula (II) and the second dianhydride represented by the following formula (IV), in which a methyl group is selected as each of $R_1$ and $R_2$, and hydrogen is selected as each of $R_3$ and $R_4$.

In a fourth experimental protocol, experimental raw materials are the first dianhydride represented by the following formula (I), the first diamine represented by the following formula (III) and the second dianhydride represented by the following formula (IV), in which a methyl group is selected as each of $R_1$ and $R_2$, and hydrogen is selected as each of $R_3$ and $R_4$.

In a fifth experimental protocol, experimental raw materials are the first dianhydride represented by the following formula (I), the first diamine represented by the following formula (II) and the second diamine represented by the following formula (V), in which a methyl group is selected as each of $R_1$ and $R_2$.

In a sixth experimental protocol, experimental raw materials are the first dianhydride represented by the following formula (I), the first diamine represented by the following formula (III) and the second diamine represented by the following formula (V), in which a methyl group is selected as each of $R_1$ and $R_2$.

In a seventh experimental protocol, experimental raw materials are the second dianhydride represented by the following formula (IV), the first diamine represented by the following formula (II) and the second diamine represented by the following formula (V), in which hydrogen is selected as each of $R_3$ and $R_4$.

In an eighth experimental protocol, experimental raw materials are the second dianhydride represented by the following formula (IV), the first diamine represented by the following formula (III) and the second diamine represented by the following formula (V), in which hydrogen is selected as each of $R_3$ and $R_4$.

In a ninth experimental protocol, experimental raw materials are the first dianhydride represented by the following formula (I), the second dianhydride represented by the following formula (IV) and the second diamine represented by the following formula (V), in which a methyl group is selected as each of $R_1$ and $R_2$, hydrogen is selected as $R_3$, and a hydroxyl group is selected as $R_4$.

(I)

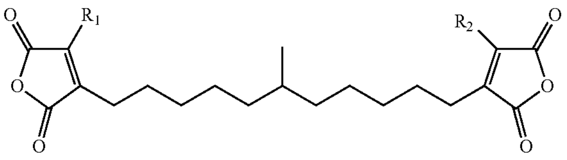

(II)

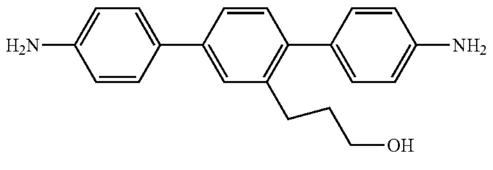

(III)

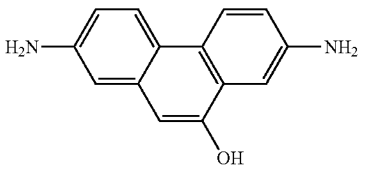

-continued (IV)

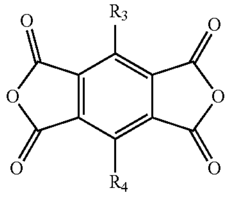

(V)

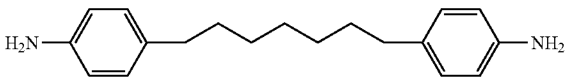

Figure 6:
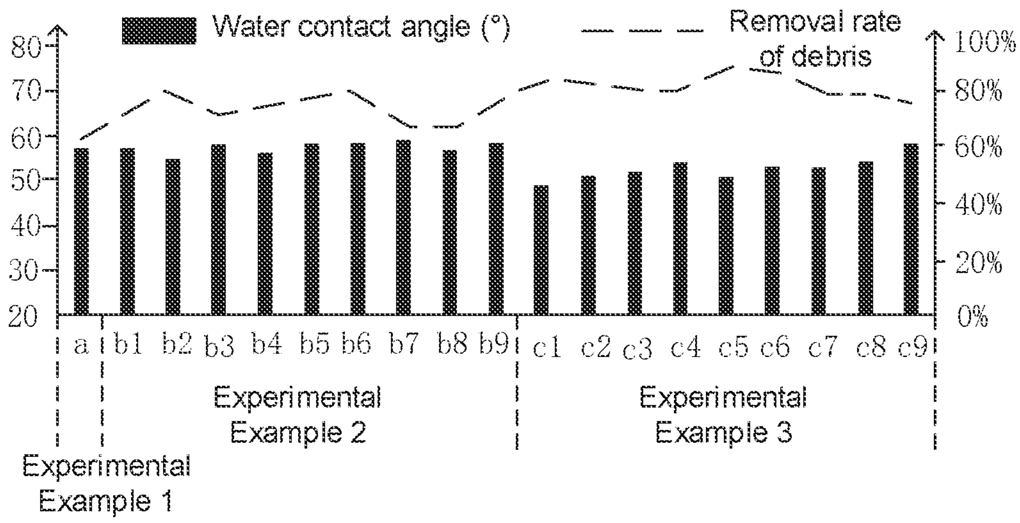
FIG. 6 is a diagram showing comparisons among the sample a, the samples b1 to b9 and the samples c1 to c9 in the aspects of the water contact angle and the debris removal rate, respectively, in accordance with some embodiments.

Water contact angles and removal rates of debris measured in the first experimental protocol to the ninth experimental protocol in Experimental Example 3 (which are marked as c1 to c9, respectively), water contact angles and removal rates of debris measured in the first experimental protocol to the ninth experimental protocol in Experimental Example 2 (which are marked as b1 to b9, respectively), and a water contact angle and a removal rate of debris measured in Experimental Example 1, are shown in Table 2 below and FIG. 6.

(I)

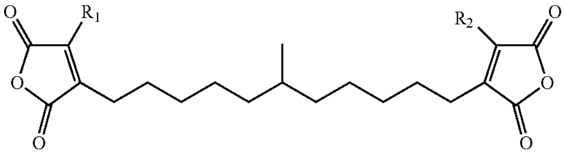

(II)

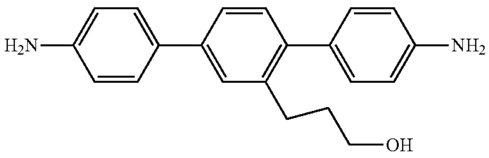

(IV)

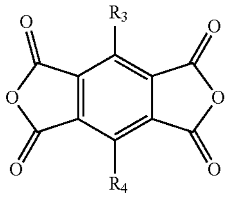

TABLE 2

| Experimental | Experimental example 1 | Experimental example 2 | | | | | | | | |
|---|---|---|---|---|---|---|---|---|---|---|
| example | a | b1 | b2 | b3 | b4 | b5 | b6 | b7 | b8 | b9 |
| Water contact angle (°) | 57 | 57 | 55 | 58 | 56 | 58 | 58 | 59 | 57 | 58 |
| Removal rate of debris (%) | 66% | 76% | 83% | 73% | 78% | 81% | 83% | 72% | 73% | 79% |
| Experimental | — | Experimental example 3 | | | | | | | | |
| example | — | c1 | c2 | c3 | c4 | c5 | c6 | c7 | c8 | c9 |
| Water contact angle (°) | — | 49 | 51 | 52 | 54 | 51 | 53 | 53 | 54 | 58 |
| Removal rate of debris (%) | — | 89% | 87% | 85% | 85% | 92% | 90% | 83% | 82% | 79% |

It can be seen from Table 2 and FIG. 6 that, in the technical solutions of the present disclosure, the hydrophilicity and hydrophobicity of the polyamic acid may be adjusted by introducing the hydrophilic group and the hydrophobic group into the first experimental protocol to the ninth experimental protocol in Experimental Example 2, so that hydrophilicity and hydrophobicity of the liquid crystal alignment film finally obtained may be adjusted, and the debris generated may be reduced by cleaning.

Experimental Example 4

In Experimental Example 4, the following experimental protocols are used. The following experimental protocols are same as the preparation method in Experimental Example 1, except that in the following experimental protocols, the first dianhydride represented by the following formula (I), the first diamine represented by the following formula (II), the first dianhydride represented by the following formula (IV) and the second diamine represented by the following formula (V) are used, in which a methyl group is selected as each of $R_1$ and $R_2$, and hydrogen is selected as each of $R_3$ and $R_4$.

-continued (V)

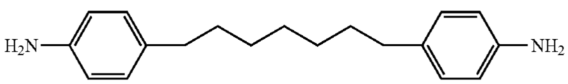

Experimental Protocol m includes a plurality of experimental groups, in which the molar percentage between the first diamine and the second diamine is 35%:15% and is fixed. In different experimental groups, ratios between the first dianhydride added and the second dianhydride added are different, and data of each experimental group is shown in Table 3 below. For data of the hardness and the toughness obtained in Experimental Group to Experimental Group 6, reference may be made Table 3.

TABLE 3

| Experimental group | Experimental group 1 | Experimental group 2 | Experimental group 3 | Experimental group 4 | Experimental group 5 | Experimental group 6 |
|---|---|---|---|---|---|---|
| Molar percentage between the first dianhydride added and the second dianhydride added | 5:45 | 10:40 | 15:35 | 20:30 | 25:25 | 45:5 |
| Hardness (μm) | 29 | 29 | 30 | 31 | 32 | 35 |
| Toughness (μN) | 430 | 450 | 486 | 512 | 527 | 555 |

It can be seen from Table 3 that, in a case where the molar percentage between the first diamine and the second diamine is fixed, as the molar percentage between the first dianhydride added and the second dianhydride added gradually increases, the hardness decreases and the toughness increases, and conversely, the toughness decreases and the hardness increases.

Experimental Protocol 2 includes a plurality of experimental groups, in which the molar percentage between the first dianhydride and the second dianhydride is 10%:40% and is fixed. In different experimental groups, ratios between the first diamine added and the second diamine added are different, and data of each experimental group is shown in Table 4 below. Water contact angles and removal rates of debris obtained in Experimental Group 1 to Experimental Group 6 are shown in FIG. 4.

TABLE 4

| Experimental group | Experimental group 1 | Experimental group 2 | Experimental group 3 | Experimental group 4 | Experimental group 5 | Experimental group 6 |
|---|---|---|---|---|---|---|
| Molar percentage between the first diamine added and the second diamine added | 5:45 | 20:30 | 25:25 | 30:20 | 35:15 | 45:5 |
| Water contact angle (°) | 56 | 54 | 53 | 52 | 52 | 50 |
| Removal rate of debris (%) | 81% | 85% | 87% | 90% | 92% | 90% |

In can be seen from Table 4 that, by proportioning the first diamine and the second diamine, hydrophilicity and hydrophobicity of a sample may be changed. Specifically, as the molar percentage between the first diamine and the second diamine increases, the hydrophilicity increases, and a measured water contact angle of the samples change from 54° to 50°. The samples are cleaned under same conditions, and the removal rates of debris before and after the cleaning changes from 85% to 92% and then to 90%. As the ratio of the first diamine to the second diamine increases, the water contact angle gradually decreases, and the removal rate of debris first increases and then decreases. This is because that, in a case where the hydrophilicity is too strong, although the debris that has been generated is easy to clean, it is easy to absorb foreign matter in the environment, thereby increasing the number of debris.

Experimental Example 5

In Experimental Example 5, the following experimental protocol is used. The following experimental protocol is same as the preparation method in Experimental Example 1, except that in the following experimental protocol, the second dianhydride represented by the following formula (IV) and the second diamine represented by the following formula (V) are used, in which hydrogen is selected as $R_3$, and a hydroxyl group is selected as $R_4$. A finally obtained sample for measuring a water contact angle and cleanness is marked as sample f, and water contact angles and removal rates of debris of the sample a and the sample f are shown in Table 5 below.

(IV)

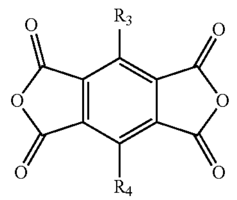

-continued (V)

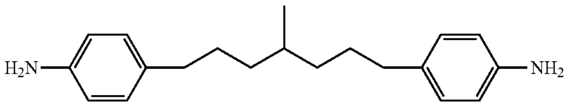

TABLE 5

| Sample number | Sample a | Sample f |
|---|---|---|
| Water contact angle (°) | 57 | 53 |
| Removal rate of debris (%) | 66% | 83% |

It can be seen from Table 5 that, for the polyamic acid provided by the present disclosure, by introducing a hydrophilic group and a hydrophobic group, and by reasonably proportioning the hydrophobic group and the hydrophilic group, the polyamic acid may have a small water contact angel, so that the removal rate of the debris may be improved, and the debris generated may be finally reduced by cleaning, and the defect of debris may be avoided.

The foregoing descriptions are merely specific implementations of the present disclosure, but the protection scope of the present disclosure is not limited thereto. Any changes or replacements that a person skilled in the art could conceive of within the technical scope of the present disclosure shall be included in the protection scope of the present disclosure.

Therefore, the protection scope of the present disclosure shall be subject to the protection scope of the claims.

What is claimed is:

1. A liquid crystal aligning agent, comprising:

at least one polymer selected from at least one of a polyamic acid and a group of polyimides obtained by ring closure of the polyamic acid, wherein the polyamic acid includes a first segment structure formed by reacting a first dianhydride represented by a following formula (I) with a first diamine represented by a following formula (II);

(I)

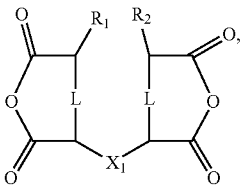

and (II)

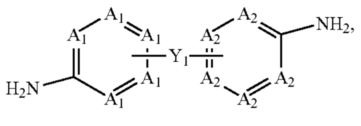

wherein $X_1$ in the first dianhydride is a first soft segment, and the first soft segment is an amorphous segment; the first soft segment is a substituted or unsubstituted alkylene segment having 10 to 20 carbon atoms, the first soft segment is selected from a hydrophobic segment or a segment including at least one hydrophobic group; and L is selected from a single bond, a double bond or a divalent or trivalent hydrocarbon group having 1 to 3 carbon atoms;

in the first diamine represented by the formula (II), $Y_1$ is selected from a substituted aromatic ring, a substituted heterocyclic ring or a substituted fused ring, in each of which at least one carbon atom is substituted; and at least one substituent group is selected from a hydrophilic group or a hydrocarbon group having 1 to 3 carbon atoms and having at least one hydrophilic group;

each of a single $A_1$ and a single $A_2$ is C, and the single $A_1$ and the single $A_2$ are both combined with $Y_1$; remaining $A_1$s and remaining $A_2$s are each independently selected from CH, CR or N, and neither of a number of Ns in the remaining $A_1$s and a number of Ns in the remaining $A_2$s is more than two; and $R_1$, $R_2$ and R are each independently selected from hydrogen or an aliphatic hydrocarbon group.

2. The liquid crystal aligning agent according to claim 1, wherein in the first diamine, $Y_1$ is bonded to a para-position of an amino group, and a benzene ring in which a single carbon atom is substituted is selected as $Y_1$, and a substituent group is an alcoholic hydroxyl group having 1 to 3 carbon atoms.

3. The liquid crystal aligning agent according to claim 1, wherein the first dianhydride has an asymmetrical structure, or the first soft segment includes asymmetrical branches.

4. The liquid crystal aligning agent according to claim 1, wherein the polyamic acid further includes a second segment structure formed by reacting a second dianhydride represented by a following formula (IV) with the first diamine;

(IV)

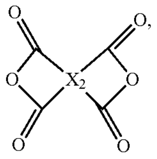

wherein $X_2$ in the second dianhydride is selected from an aliphatic ring, an aromatic ring, a heterocyclic ring or a fused ring.

5. The liquid crystal aligning agent according to claim 4, wherein a following formula is selected as a structure of $X_2$, in which $R_3$ and $R_4$ are each independently selected from hydrogen or the aliphatic hydrocarbon group;

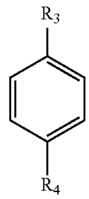

;

and/or a molar ratio of the first dianhydride to the second dianhydride is in a range from 10:90 to 90:10, inclusive.

6. The liquid crystal aligning agent according to claim 1, wherein the polyamic acid further includes a third segment structure formed by reacting a second diamine represented by a following formula (V) with the first dianhydride;

(V)

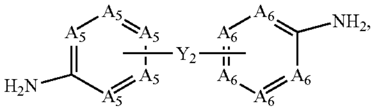

wherein $Y_2$ in the second diamine is a second soft segment; the second soft segment is a substituted or unsubstituted alkylene segment having 5 to 12 carbon atoms; and each of a single $A_5$ and a single $A_6$ is C, and the single $A_5$ and the single $A_6$ are both combined with $Y_2$; remaining $A_5$s and remaining $A_6$s are each independently selected from CH, CR or N, neither of a number of Ns in the remaining $A_5$s and a number of Ns in the remaining $A_6$s is more than two, and R is selected from hydrogen or the aliphatic hydrocarbon group.

7. The liquid crystal aligning agent according to claim 6, wherein the at least one substituent group in Y1 is the hydrophilic group, and the second soft segment is selected from a hydrophobic segment, a segment including at least one hydrophobic group, the hydrophilic segment or the segment including the at least one hydrophilic group, or the at least one substituent group in Y1 is the segment including the at least one hydrophilic group, the second soft segment is selected from the hydrophilic segment, the segment including the at least one hydrophilic group, the hydrophobic segment or the segment including the at least one hydrophobic group.

8. The liquid crystal aligning agent according to claim 6, wherein a molar ratio of the first diamine to the second diamine is in a range from 10:90 to 90:10, inclusive.

9. A liquid crystal alignment film formed by using the liquid crystal aligning agent according to claim 1.

10. The liquid crystal alignment film according to claim 9, wherein hardness of the liquid crystal alignment film is characterized by a depth at which a pricking needle pricks into the liquid crystal alignment film under a preset pressure, and the hardness of the liquid crystal alignment film satisfies that a value thereof is less than or equal to 45 μm under the preset pressure of 150 μN; and/or toughness of the liquid crystal alignment film is characterized by a pressure corresponding to an abrupt depth change of a pricking needle in a thickness direction of the liquid crystal alignment film, and a value of the toughness of the liquid crystal alignment film is greater than 390 μN; and/or the liquid crystal aligning agent includes a hydrophilic segment and/or a hydrophilic group, a water contact angle of the liquid crystal alignment film is less than or equal to 58 degrees; and/or a molar percentage between the first diamine and a second diamine included in the liquid crystal aligning agent is 35%:15%, as a ratio between the first dianhydride and a second dianhydride included in the liquid crystal aligning agent increases, hardness of the liquid crystal alignment film decreases, and toughness of the liquid crystal alignment film increases; and/or a molar percentage between the first dianhydride and a second dianhydride included in the liquid crystal aligning agent is 10%:40%, and $Y_2$ in a second diamine is a hydrophobic segment, as a ratio between the first diamine and the second diamine included in the liquid crystal aligning agent increases, a water contact angle of the liquid crystal alignment film decreases.

11. A display substrate, comprising:

a base substrate; and a liquid crystal alignment film disposed on the base substrate, the liquid crystal alignment film including a polyimide obtained after baking the liquid crystal aligning agent according to claim 1.

12. A liquid crystal aligning agent, comprising:

at least one polymer selected from at least one of a polyamic acid and a group of polyimides obtained by ring closure of the polyamic acid, wherein the polyamic acid includes a first segment structure formed by a first dianhydride represented by a following formula (I) and a first diamine represented by a following formula (II), a second segment structure formed by a second dianhydride represented by a following formula (IV) and the first diamine, a third segment structure formed by a second diamine represented by a following formula (V) and the first dianhydride, and a fourth segment structure formed by the second diamine represented by the following formula (V) and the second dianhydride;

(I)

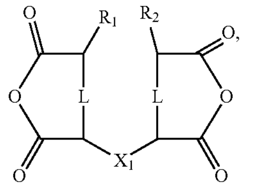

(II)

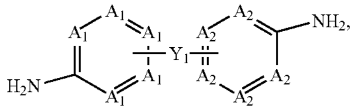

(IV)

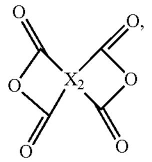

and (V)

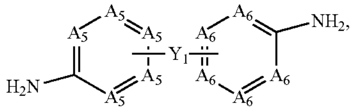

wherein $X_1$ in the first dianhydride is a first soft segment, $Y_2$ in the second diamine is a second soft segment, and at least one of the first soft segment and the second soft segment is an amorphous segment; the first soft segment is a substituted or unsubstituted alkylene segment having 10 to 20 carbon atoms, the second soft segment is a substituted or unsubstituted alkylene segment having 5 to 12 carbon atoms, and the second soft segment is selected from a hydrophobic segment or a segment including at least one hydrophobic group; and L in the first dianhydride is selected from a single bond, a double bond or a divalent or trivalent hydrocarbon group having 1 to 3 carbon atoms;

$X_2$ in the second dianhydride is selected from a substituted or unsubstituted aliphatic ring, a substituted or unsubstituted aromatic ring, a substituted or unsubstituted heterocyclic ring, or a substituted or unsubstituted fused ring;

in the first diamine represented by formula (II), $Y_1$ is selected from a substituted aromatic ring, a substituted heterocyclic ring or a substituted fused ring, in each of which at least one carbon atom is substituted; and at least one substituent group is selected from a hydrophilic group or a hydrocarbon group having 1 to 3 carbon atoms and having at least one hydrophilic group;

each of a single $A_1$ and a single $A_2$ is C, and the single $A_1$ and the single $A_2$ are both combined with $Y_1$; remaining Als and remaining $A_2$s are each independently selected from CH, CR or N, and neither of a number of Ns in the remaining $A_1$s and a number of Ns in the remaining $A_2$s is more than two;

in the second diamine, each of a single $A_5$ and a single $A_6$ is C, and the single $A_5$ and the single $A_6$ are both combined with $Y_2$; remaining $A_5$s and remaining $A_6$s are each independently selected from CH, CR or N, and neither of a number of Ns in the remaining $A_5$s and a number of Ns in the remaining $A_6$s is more than two; and $R_1$, $R_2$ and R are each independently selected from hydrogen or an aliphatic hydrocarbon group.

13. The liquid crystal aligning agent according to claim 12, wherein if $X_2$ is selected from an unsubstituted aliphatic ring, an unsubstituted aromatic ring, an unsubstituted heterocyclic ring or an unsubstituted fused ring, then the at least one substituent group in $Y_1$ is the hydrophilic group, and the first soft segment is selected from the hydrophobic segment, the segment including the at least one hydrophobic group, the hydrophilic segment or the segment including the at least one hydrophilic group;

if $X_2$ is selected from a substituted aliphatic ring, a substituted aromatic ring, substituted heterocyclic ring or a substituted fused ring, then the at least one substituent group in $Y_1$ is the hydrophilic group, and the at least one substituent group in $X_2$ is selected from the hydrophilic group or the hydrophobic group, and the first soft segment is selected from the hydrophobic segment, the segment including the at least one hydrophobic group, the hydrophilic segment or the segment including the at least one hydrophilic group, or the at least one substituent group in $Y_1$ is the segment including the at least one hydrophilic group, the at least one substituent group in $X_2$ and the first soft segment are each selected from the hydrophilic segment, the segment including the at least one hydrophilic group, the hydrophobic segment or the segment including the at least one hydrophobic group.

14. The liquid crystal aligning agent according to claim 12, wherein in the first diamine, $Y_1$ is bonded to a para-position of an amino group, and a benzene ring in which a carbon atom is substituted is selected as $Y_1$, and a substituent group is an alcoholic hydroxyl group having 1 to 3 carbon atoms.

15. A liquid crystal alignment film formed by using the liquid crystal aligning agent according to claim 12.

16. The liquid crystal alignment film according to claim 15, wherein hardness of the liquid crystal alignment film is characterized by a depth at which a pricking needle pricks into the liquid crystal alignment film under a preset pressure, and the hardness of the liquid crystal alignment film satisfies that a value thereof is less than or equal to 45 μm under the preset pressure of 150 μN; and/or toughness of the liquid crystal alignment film is characterized by a pressure corresponding to an abrupt depth change of a pricking needle in a thickness direction of the liquid crystal alignment film, and a value of the toughness of the liquid crystal alignment film is greater than 390 μN; and/or the liquid crystal aligning agent includes a hydrophilic segment and/or a hydrophilic group, a water contact angle of the liquid crystal alignment film is less than or equal to 58 degrees; and/or a molar percentage between the first diamine and the second diamine included in the liquid crystal aligning agent is 35%:15%, as a ratio between the first dianhydride and the second dianhydride included in the liquid crystal aligning agent increases, hardness of the liquid crystal alignment film decreases, and toughness of the liquid crystal alignment film increases; and/or a molar percentage between the first dianhydride and the second dianhydride included in the liquid crystal aligning agent is 10%:40%, and $Y_2$ in the second diamine is a hydrophobic segment, as a ratio between the first diamine and the second diamine included in the liquid crystal aligning agent increases, a water contact angle of the liquid crystal alignment film decreases.

17. A display substrate, comprising:

a base substrate; and a liquid crystal alignment film disposed on the base substrate, the liquid crystal alignment film including a polyimide obtained after baking the liquid crystal aligning agent according to claim 12.

* * * * *